(12) United States Patent
Jackson

(10) Patent No.: US 11,224,463 B2
(45) Date of Patent: Jan. 18, 2022

(54) DYNAMIC STABILIZATION CONNECTING MEMBER WITH PRE-TENSIONED FLEXIBLE CORE MEMBER

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

(21) Appl. No.: 15/943,257

(22) Filed: Apr. 2, 2018

(65) Prior Publication Data

US 2018/0221063 A1 Aug. 9, 2018

Related U.S. Application Data

(63) Continuation of application No. 15/197,247, filed on Jun. 29, 2016, now Pat. No. 9,931,139, which is a continuation of application No. 13/317,158, filed on Oct. 11, 2011, now abandoned, which is a continuation of application No. 12/459,492, filed on Jul. 1, 2009, now Pat. No. 8,366,745, which is a continuation-in-part of application No. 12/156,260, filed on May 30, 2008, now Pat. No. 7,951,170, and a continuation-in-part of application No. 12/148,465, filed on Apr. 18, 2008, now Pat. No. 10,258,382, which is a continuation-in-part of application No. 12/006,460, filed on Jan. 3, 2008, now Pat. No. 8,475,498.

(60) Provisional application No. 61/137,743, filed on Aug. 1, 2008, provisional application No. 61/134,480, filed on Jul. 10, 2008, provisional application No. 60/994,068, filed on Sep. 17, 2007, provisional application No. 60/932,567, filed on May 31, 2007, provisional application No. 60/927,111, filed on May 1, 2007, provisional application No. 60/922,465, filed on Apr. 9, 2007, provisional application No.

(Continued)

(51) Int. Cl.
*A61B 17/70* (2006.01)

(52) U.S. Cl.
CPC ........ *A61B 17/7026* (2013.01); *A61B 17/702* (2013.01); *A61B 17/7004* (2013.01); *A61B 17/705* (2013.01); *A61B 17/7037* (2013.01); *A61B 17/7049* (2013.01)

(58) Field of Classification Search
CPC ............................................ A61B 17/70–7046
See application file for complete search history.

(56) References Cited

U.S. PATENT DOCUMENTS

| 5,171,279 A | 12/1992 | Mathews |
| D346,217 S | 4/1994 | Sparker et al. |

(Continued)

OTHER PUBLICATIONS

U.S. Appl. No. 15/883,794, filed Jan. 30, 2018, Jackson.

(Continued)

*Primary Examiner* — Eduardo C Robert
*Assistant Examiner* — Steven J Cotroneo
(74) *Attorney, Agent, or Firm* — Polsinelli PC

(57) ABSTRACT

A dynamic longitudinal connecting member assembly includes an anchor member having an integral or otherwise fixed elongate core of circular or non-circular cross-section. The core is pre-tensioned and extends through at least one elastic spacer and at least one outer sleeve. The anchor member and the outer sleeve each attach to at least one bone anchor. In operation, the core is held in tension by the spacer.

20 Claims, 14 Drawing Sheets

Related U.S. Application Data

60/898,870, filed on Feb. 1, 2007, provisional application No. 60/880,969, filed on Jan. 18, 2007.

(56) References Cited

U.S. PATENT DOCUMENTS

| | | | |
|---|---|---|---|
| 5,569,253 A * | 10/1996 | Farris | A61B 17/8861 |
| | | | 606/103 |
| 6,132,431 A | 10/2000 | Nilsson et al. | |
| 6,248,106 B1 | 6/2001 | Ferree | |
| 6,251,112 B1 | 6/2001 | Jackson | |
| 6,280,442 B1 | 8/2001 | Barker et al. | |
| 6,290,700 B1 | 9/2001 | Schmotzer | |
| 6,565,565 B1 | 5/2003 | Yuan et al. | |
| 6,997,927 B2 | 2/2006 | Jackson | |
| 7,713,288 B2 | 5/2010 | Timm et al. | |
| 7,815,665 B2 | 10/2010 | Jahng et al. | |
| 7,828,825 B2 | 11/2010 | Bruneau et al. | |
| 7,842,072 B2 | 11/2010 | Dawson | |
| 7,901,437 B2 | 3/2011 | Jackson | |
| 7,988,710 B2 | 8/2011 | Jahng et al. | |
| 8,029,544 B2 | 10/2011 | Hested et al. | |
| 8,114,133 B2 | 2/2012 | Logan | |
| 8,128,667 B2 | 3/2012 | Jackson | |
| 8,157,843 B2 | 4/2012 | Biederman et al. | |
| 8,292,926 B2 | 10/2012 | Jackson | |
| 8,366,745 B2 | 2/2013 | Jackson | |
| 8,465,526 B2 | 6/2013 | Friedrich et al. | |
| 9,101,404 B2 | 8/2015 | Jackson | |
| 9,439,683 B2 | 9/2016 | Jackson | |
| 9,451,989 B2 | 9/2016 | Jackson | |
| 9,668,771 B2 | 6/2017 | Jackson | |
| 9,861,394 B2 | 1/2018 | Jackson | |
| 9,956,002 B2 | 5/2018 | Jackson | |
| 2002/0035366 A1 | 3/2002 | Walder et al. | |
| 2002/0055740 A1 | 5/2002 | Lieberman | |
| 2002/0107570 A1 | 8/2002 | Sybert et al. | |
| 2002/0116001 A1 | 8/2002 | Schafer | |
| 2002/0116065 A1 | 8/2002 | Jackson | |
| 2002/0198526 A1 | 12/2002 | Shaolian et al. | |
| 2003/0083657 A1 | 5/2003 | Drewry et al. | |
| 2003/0212398 A1 | 11/2003 | Jackson | |
| 2004/0049190 A1 | 3/2004 | Biederman et al. | |
| 2004/0138662 A1 | 7/2004 | Landry et al. | |
| 2004/0143265 A1 | 7/2004 | Landry et al. | |
| 2004/0167523 A1 | 8/2004 | Jackson | |
| 2004/0172032 A1 | 9/2004 | Jackson | |
| 2004/0215191 A1 | 10/2004 | Kitchen | |
| 2004/0236327 A1 | 11/2004 | Paul et al. | |
| 2004/0236328 A1 | 11/2004 | Paul et al. | |
| 2005/0010220 A1 | 1/2005 | Casutt et al. | |
| 2005/0085815 A1 | 4/2005 | Harms et al. | |
| 2005/0131407 A1 | 6/2005 | Sicvol et al. | |
| 2005/0149020 A1 | 7/2005 | Jahng | |
| 2005/0203514 A1 * | 9/2005 | Jahng | A61B 17/7757 |
| | | | 606/263 |
| 2005/0203517 A1 | 9/2005 | Jahng et al. | |
| 2005/0277919 A1 | 12/2005 | Slivka et al. | |
| 2005/0277920 A1 | 12/2005 | Slivka et al. | |
| 2005/0277922 A1 | 12/2005 | Trieu et al. | |
| 2005/0277932 A1 | 12/2005 | Farris | |
| 2005/0288671 A1 | 12/2005 | Yuan et al. | |
| 2005/0288672 A1 | 12/2005 | Ferree | |
| 2006/0025767 A1 | 2/2006 | Khalili | |
| 2006/0036240 A1 | 2/2006 | Colleran et al. | |
| 2006/0058788 A1 | 3/2006 | Hammer et al. | |
| 2006/0064090 A1 | 3/2006 | Park | |
| 2006/0079894 A1 | 4/2006 | Colleran et al. | |
| 2006/0142760 A1 | 6/2006 | McDonnell | |
| 2006/0149238 A1 | 7/2006 | Sherman et al. | |
| 2006/0241602 A1 | 10/2006 | Jackson | |
| 2006/0241769 A1 | 10/2006 | Gordon et al. | |
| 2006/0247635 A1 | 11/2006 | Gordon et al. | |
| 2006/0247779 A1 | 11/2006 | Gordon et al. | |
| 2006/0264937 A1 * | 11/2006 | White | A61B 17/702 |
| | | | 606/257 |
| 2007/0005063 A1 | 1/2007 | Bruneau et al. | |
| 2007/0032123 A1 | 2/2007 | Timm et al. | |
| 2007/0100341 A1 | 5/2007 | Reglos et al. | |
| 2007/0118123 A1 | 5/2007 | Strausbaugh et al. | |
| 2007/0123864 A1 | 5/2007 | Walder et al. | |
| 2007/0129729 A1 | 6/2007 | Petit et al. | |
| 2007/0191841 A1 | 8/2007 | Justis et al. | |
| 2007/0233064 A1 | 10/2007 | Holt | |
| 2007/0233075 A1 | 10/2007 | Dawson | |
| 2007/0270821 A1 | 11/2007 | Trieu et al. | |
| 2007/0270840 A1 | 11/2007 | Chin et al. | |
| 2007/0276380 A1 * | 11/2007 | Jahng | A61B 17/3468 |
| | | | 606/86 A |
| 2007/0288011 A1 | 12/2007 | Logan | |
| 2008/0021469 A1 | 1/2008 | Holt | |
| 2008/0051787 A1 | 2/2008 | Remington et al. | |
| 2008/0086125 A1 | 4/2008 | Molz et al. | |
| 2008/0086130 A1 | 4/2008 | Lake | |
| 2008/0161857 A1 | 7/2008 | Hestad et al. | |
| 2008/0183213 A1 | 7/2008 | Veldman et al. | |
| 2008/0234691 A1 | 9/2008 | Schwab | |
| 2008/0234737 A1 | 9/2008 | Boschert | |
| 2008/0234744 A1 | 9/2008 | Zylber et al. | |
| 2008/0262551 A1 | 10/2008 | Rice et al. | |
| 2008/0262553 A1 | 10/2008 | Hawkins et al. | |
| 2008/0275504 A1 | 11/2008 | Bonin et al. | |
| 2008/0294198 A1 | 11/2008 | Jackson | |
| 2008/0319482 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1 | 1/2009 | Hestad et al. | |
| 2009/0036924 A1 | 2/2009 | Egli et al. | |
| 2009/0054932 A1 | 2/2009 | Butler et al. | |
| 2009/0082815 A1 | 3/2009 | Zylber et al. | |
| 2009/0088799 A1 | 4/2009 | Yeh | |
| 2009/0093846 A1 | 4/2009 | Hestad | |
| 2009/0099606 A1 | 4/2009 | Hestad et al. | |
| 2009/0105757 A1 | 4/2009 | Gimbel et al. | |
| 2009/0105758 A1 | 4/2009 | Gimbel et al. | |
| 2009/0177231 A1 | 7/2009 | Kiester | |
| 2009/0198280 A1 | 8/2009 | Spratt et al. | |
| 2009/0204152 A1 | 8/2009 | Blain | |
| 2009/0228045 A1 | 9/2009 | Hayes et al. | |
| 2009/0240285 A1 | 9/2009 | Friedrich et al. | |
| 2009/0240286 A1 | 9/2009 | Friedrich et al. | |
| 2009/0259257 A1 | 10/2009 | Prevost | |
| 2009/0275983 A1 | 11/2009 | Veldman et al. | |
| 2009/0299411 A1 | 12/2009 | Laskowitz et al. | |
| 2010/0010542 A1 | 1/2010 | Jackson | |
| 2010/0010543 A1 | 1/2010 | Jackson | |
| 2010/0036423 A1 | 2/2010 | Hayes | |
| 2010/0137912 A1 | 6/2010 | Alcock et al. | |
| 2010/0174319 A1 | 7/2010 | Jackson | |
| 2010/0211105 A1 | 8/2010 | Moumene et al. | |
| 2010/0228292 A1 | 9/2010 | Arnold et al. | |
| 2010/0331887 A1 | 12/2010 | Jackson et al. | |
| 2011/0004222 A1 | 1/2011 | Biedermann et al. | |
| 2011/0301644 A1 | 12/2011 | Belliard | |
| 2012/0035660 A1 | 2/2012 | Jackson | |
| 2012/0053636 A1 | 3/2012 | Schmocker | |
| 2012/0221054 A1 | 8/2012 | Jackson | |
| 2013/0123853 A1 | 5/2013 | Seme et al. | |
| 2013/0197582 A1 | 8/2013 | Prevost et al. | |
| 2014/0018857 A1 | 1/2014 | Jackson | |
| 2014/0039555 A1 | 2/2014 | Jackson | |
| 2014/0222076 A1 | 8/2014 | Jackson | |
| 2014/0343610 A1 | 11/2014 | Jackson | |
| 2014/0379030 A1 | 12/2014 | Jackson | |
| 2015/0216567 A1 | 8/2015 | Trautwein et al. | |
| 2015/0230827 A1 | 8/2015 | Zylber et al. | |
| 2015/0320449 A1 | 11/2015 | Jackson | |
| 2016/0310169 A1 | 10/2016 | Jackson et al. | |
| 2016/0310171 A1 | 10/2016 | Jackson | |
| 2016/0346010 A1 | 12/2016 | Jackson | |
| 2016/0354118 A1 | 12/2016 | Belliard et al. | |
| 2016/0354120 A1 | 12/2016 | Jackson | |
| 2017/0100165 A1 | 4/2017 | Jackson | |
| 2017/0231662 A1 | 8/2017 | Jackson | |
| 2017/0340362 A1 | 11/2017 | Jackson | |

(56) References Cited

U.S. PATENT DOCUMENTS

2018/0132901 A1    5/2018   Jackson et al.
2018/0168693 A1    6/2018   Jackson et al.
2018/0185068 A1    7/2018   Jackson
2018/0243008 A1    8/2018   Jackson
2019/0183534 A1    6/2019   Jackson
2019/0231395 A1    8/2019   Jackson
2019/0239925 A1    8/2019   Jackson
2019/0365427 A1    8/2019   Jackson

OTHER PUBLICATIONS

Overlap. Merriam-Webster, accessed Apr. 13, 2015 http://www.merriam-webster.com/dictionary/overlap.
U.S. Appl. No. 15/918,181, filed Mar. 12, 2018, Jackson.
U.S. Appl. No. 16/677,981, filed Nov. 8, 2019, Jackson.

* cited by examiner

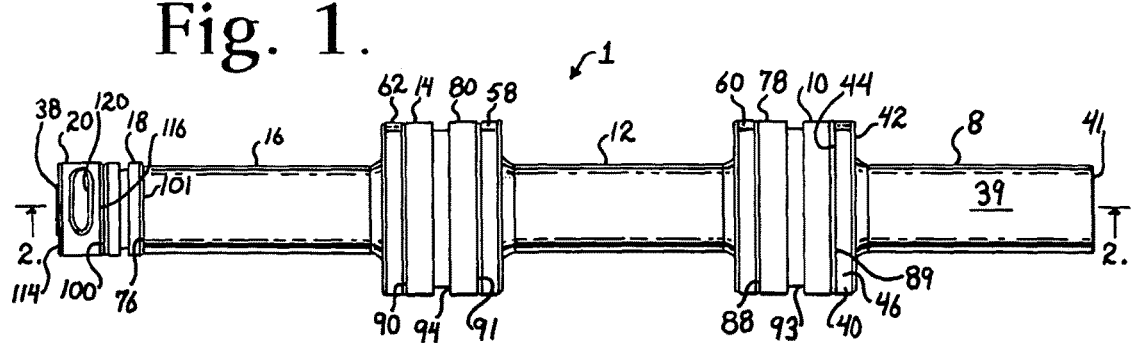
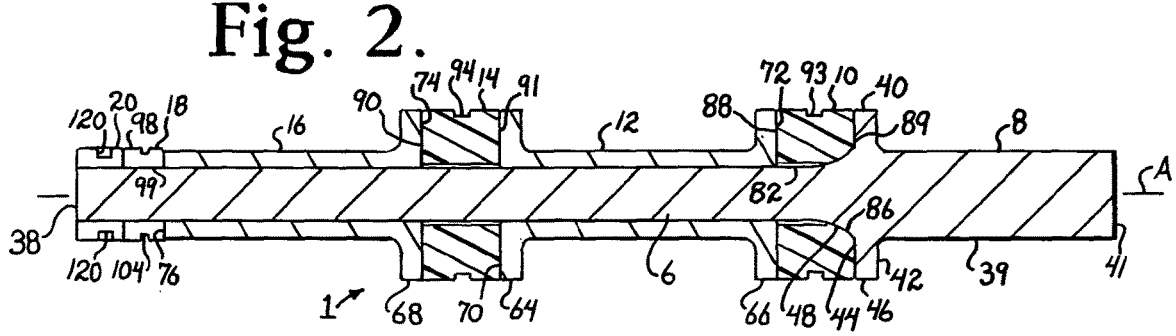
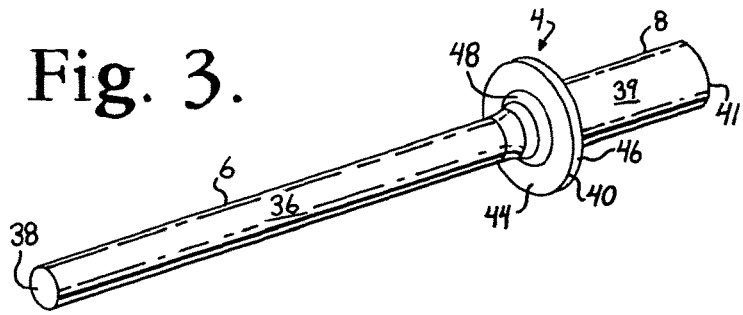
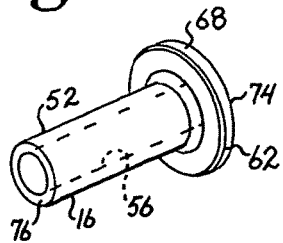
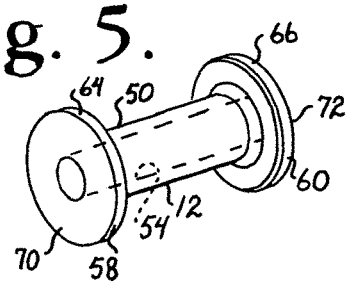

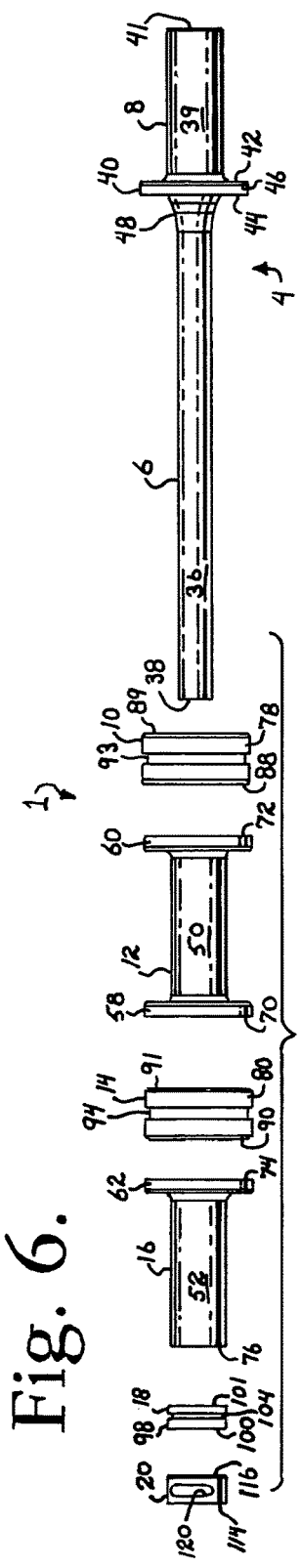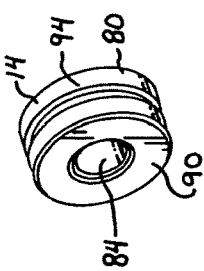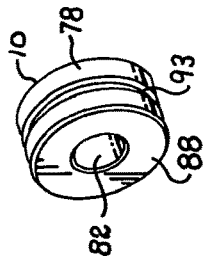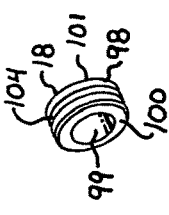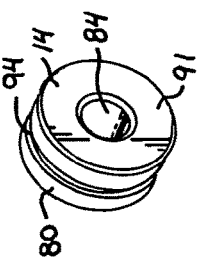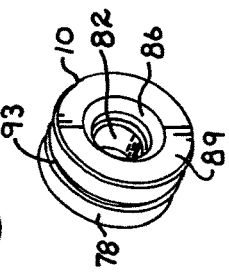

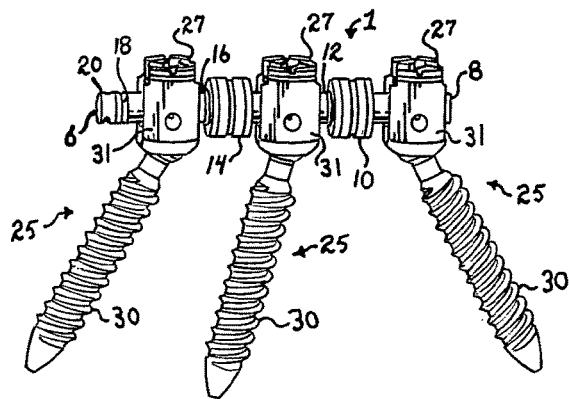
Fig. 13.
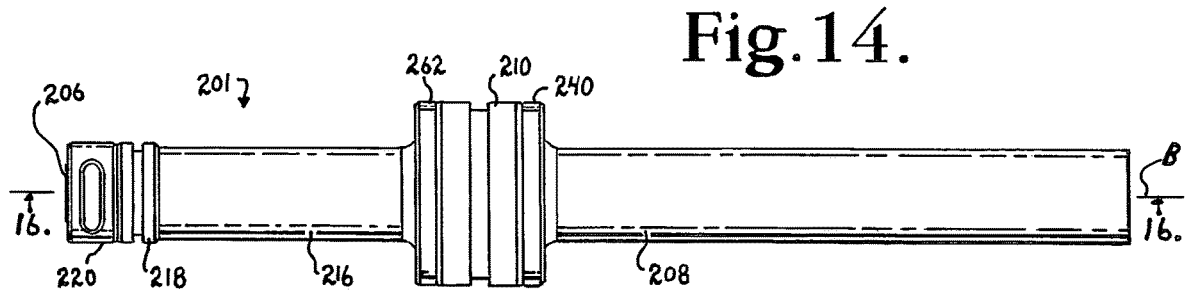
Fig. 14.
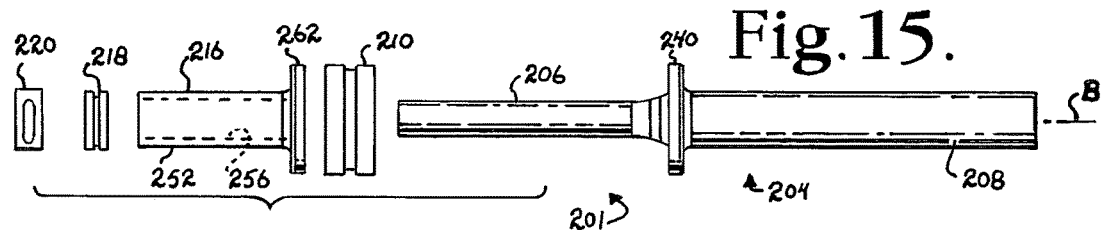
Fig. 15.
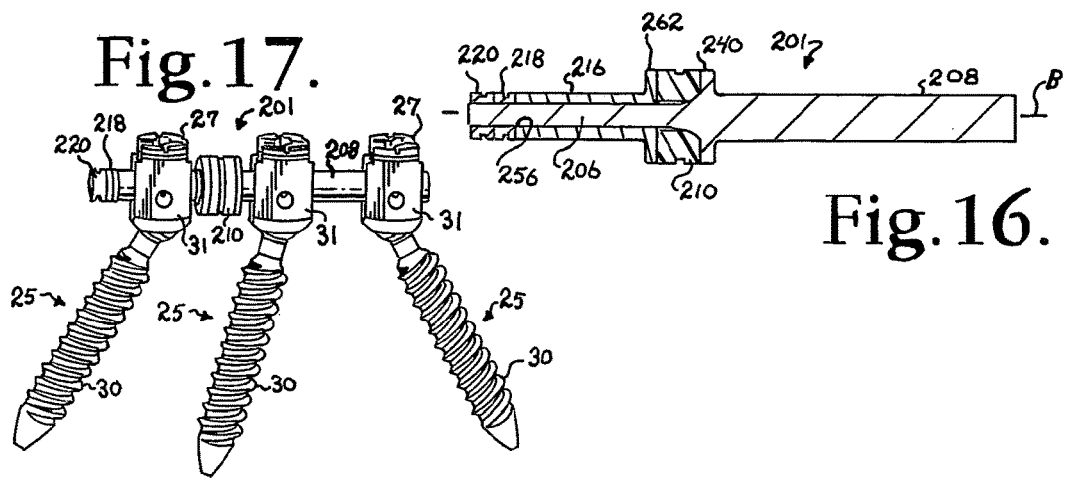
Fig. 17.
Fig. 16.

Fig. 18.
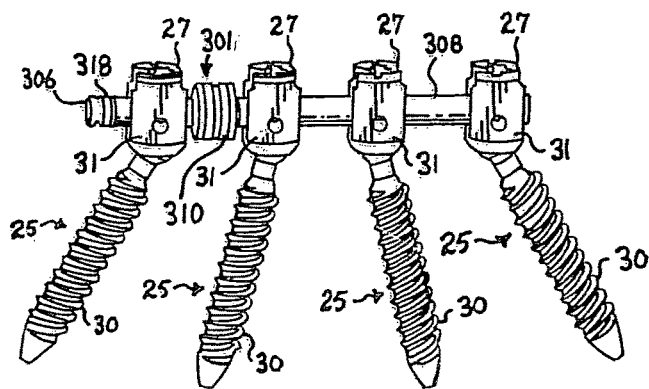
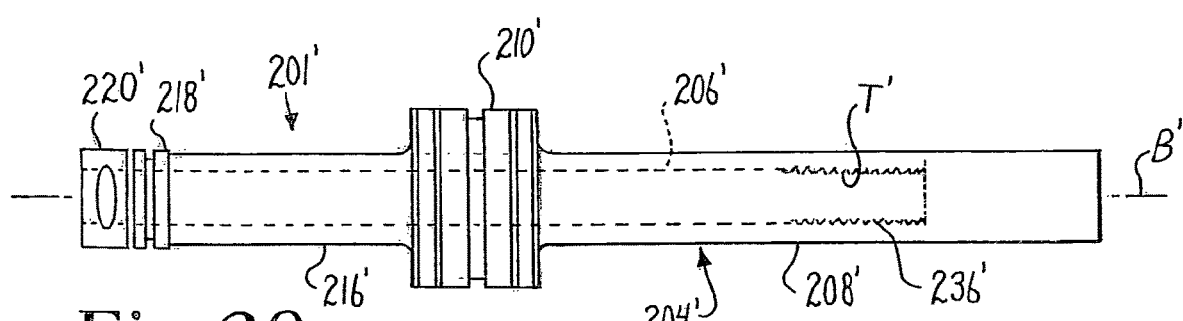
Fig. 20.
Fig. 19.
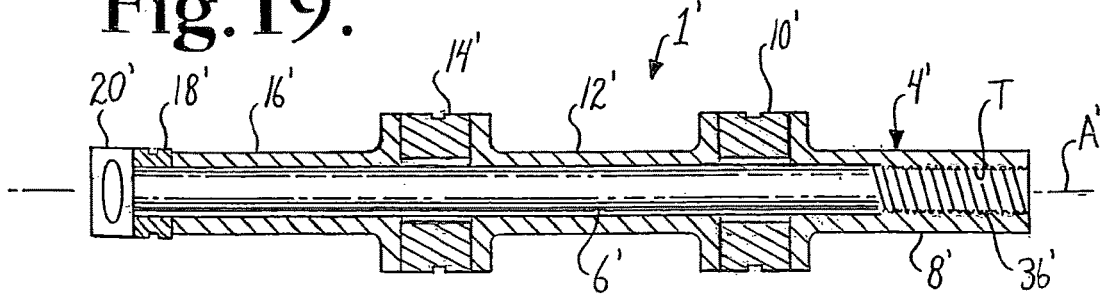

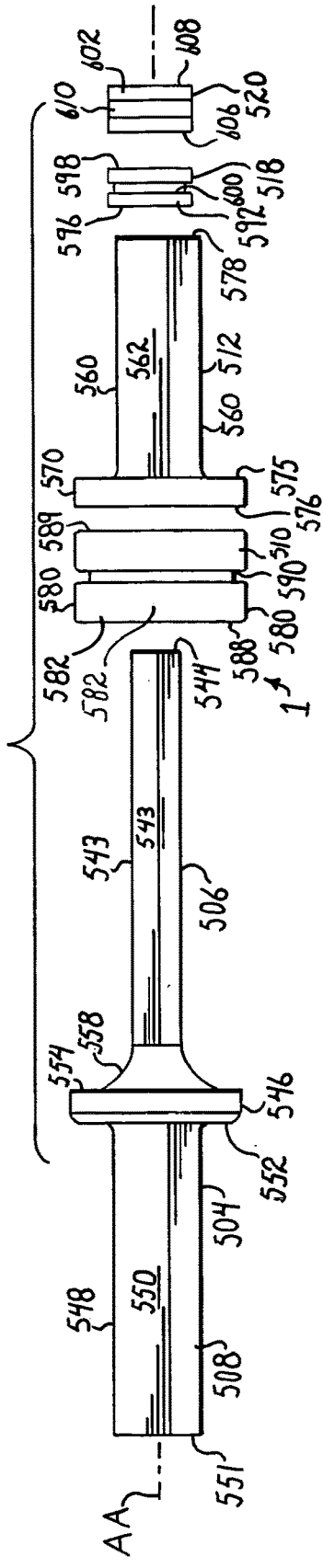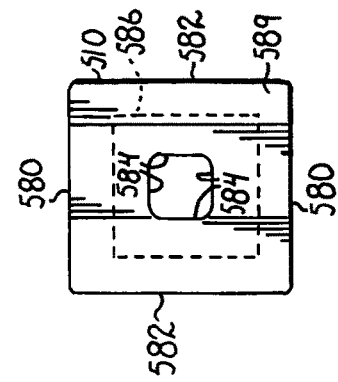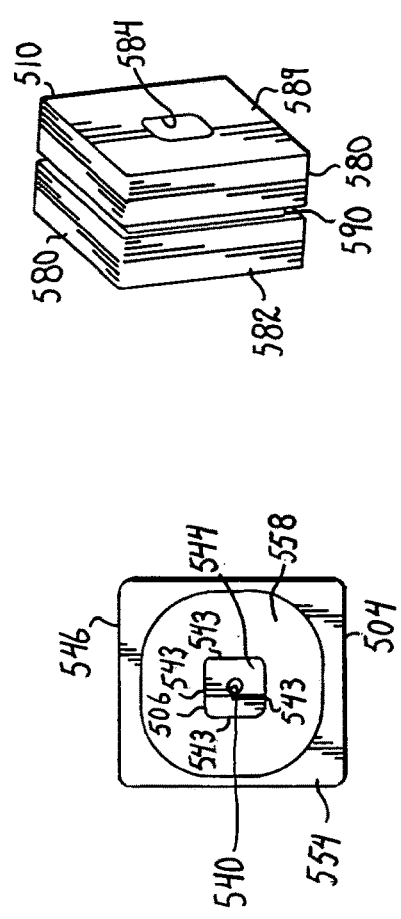

Fig.38.
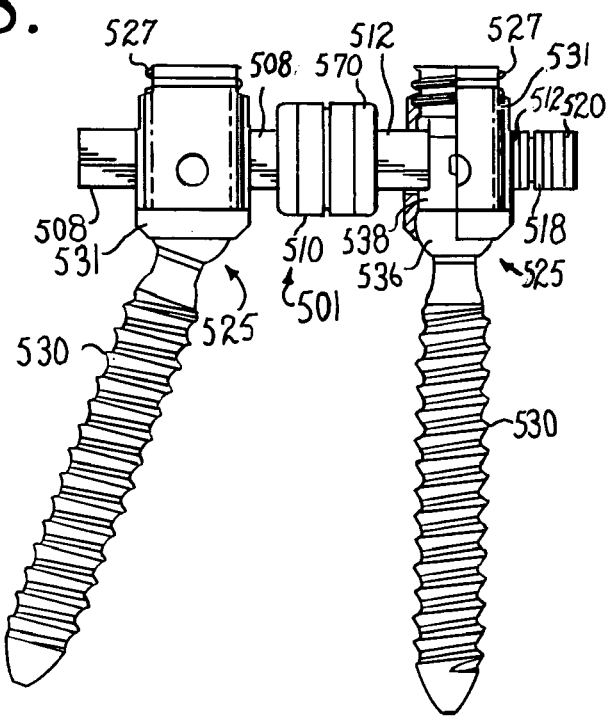
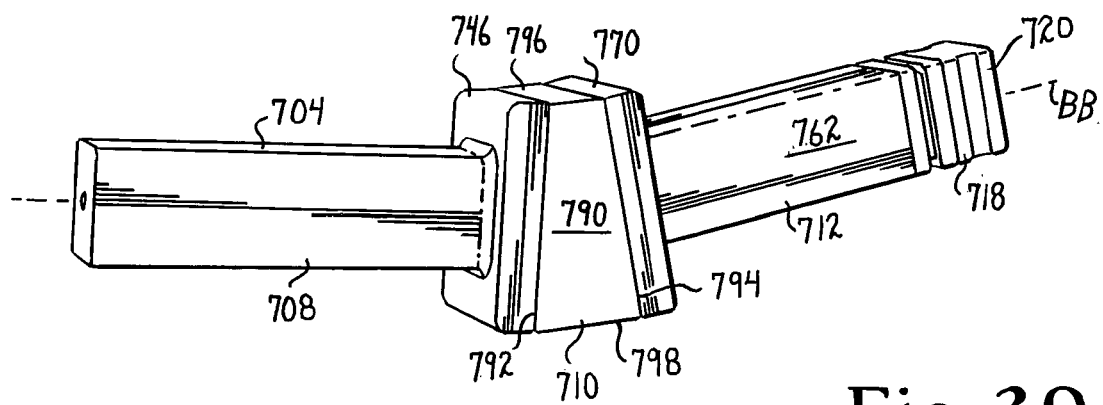
Fig.39.

DYNAMIC STABILIZATION CONNECTING MEMBER WITH PRE-TENSIONED FLEXIBLE CORE MEMBER

CROSS-REFERENCE TO RELATED APPLICATIONS

This application is a continuation of U.S. application Ser. No. 15/197,247, filed on Jun. 29, 2016, which is a continuation of U.S. application Ser. No. 13/317,158, filed on Oct. 11, 2011, now abandoned, which is a continuation of U.S. application Ser. No. 12/459,492, filed Jul. 1, 2009, now U.S. Pat. No. 8,366,745. U.S. application Ser. No. 12/459,492 claims the benefit of U.S. Provisional Application No. 61/137,743, filed Aug. 1, 2008 and U.S. Provisional Application No. 61/134,480, filed Jul. 10, 2008. U.S. application Ser. No. 12/459,492 is a continuation-in-part of U.S. application Ser. No. 12/156,260, filed May 30, 2008, now U.S. Pat. No. 7,951,170, which claims the benefit of U.S. Provisional Application No. 60/994,068, filed Sep. 17, 2007, and U.S. Provisional Application No. 60/932,567, filed May 31, 2007. U.S. application Ser. No. 12/459,492 is also a continuation-in-part of U.S. application Ser. No. 12/148,465, filed Apr. 18, 2008, which claims the benefit of U.S. Provisional Application No. 60/927,111, filed May 1, 2007. U.S. application Ser. No. 12/148,465 is also a continuation in part of U.S. application Ser. No. 12/006,460 filed Jan. 3, 2008, now U.S. Pat. No. 8,475,498, which claims the benefit of U.S. Provisional Application No. 60/922,465, filed Apr. 9, 2007, U.S. Provisional Application No. 60/898,870, filed Feb. 1, 2007, and U.S. Provisional Application No. 60/880,969, filed Jan. 18, 2007, all of which are incorporated by reference herein.

BACKGROUND OF THE INVENTION

The present invention is directed to dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the cord or strand in the bone anchors. Although flexible, the cords or strands utilized in such systems do not allow for elastic distraction of the system once implanted because the cord or strand must be stretched or pulled to maximum tension in order to provide a stable, supportive system.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone attachment structures or anchors provide dynamic, protected motion of the spine. A longitudinal connecting member assembly according to the invention has an inner pre-tensioned core of circular or non-circular cross-section that is integral or otherwise fixed to a first bone anchor attachment portion. At least one elastic spacer surrounds the core and is slidable along the core at a location between a pair of adjacent bone anchors. At least one outer sleeve also surrounds the core and is in sliding relationship with the core. The outer sleeve also engages at least one bone anchor. The inner core and outer elastic spacer cooperate dynamically, with the outer sleeve being in compression while the core is in tension. The assembly may further include an elastic end bumper that also is in compression and places distractive force on the core.

In one embodiment, an improved medical implant assembly having at least two bone anchor attachment structures cooperating with a longitudinal connecting member is provided, including an anchor member portion that is in engagement with one of the at least two bone anchor attachment structures, at least one compressible outer spacer, and at least one sleeve. The anchor member portion has a pre-tensioned member portion of reduced diameter that extends from an end thereof. The pre-tensioned member portion is received in the spacer, and the spacer is positioned between the at least two bone anchor attachment structures. The pre-tensioned member portion is also received within the sleeve and in slidable relationship therewith. The sleeve is in engagement with the other of the at least two bone anchor attachment structures. The improvement may further include an elastic bumper that engages the sleeve and receives the pre-tensioned member portion therein. The improvement may further include a fixation structure that is secured to the pre-tensioned member portion at an end thereof opposite the anchor member portion.

In another embodiment, an improved medical implant assembly having at least two bone attachment structures cooperating with a longitudinal connecting member is provided, the improvement wherein the longitudinal connecting member includes an anchor member portion in engagement with one of the at least two bone attachment structures, the anchor member portion having a pre-tensioned bendable core extension of reduced diameter along a length thereof, the core extension attached to and extending from the anchor member portion and having a linear and a non-linear configuration; at least one compressible outer spacer, the core extension being received in the spacer, the spacer being positioned between the at least two bone attachment structures; and at least one sleeve, the core extension being received within the sleeve and in slidable relationship therewith, the sleeve being in engagement with the other of the at least two bone attachment structures.

In yet another embodiment, an improved medical implant assembly having at least two bone anchor attachment structures cooperating with a longitudinal connecting member is provided, the improvement wherein the longitudinal connecting member includes an anchor member portion in engagement with one of the at least two bone anchor attachment structures, the anchor member portion having a pre-tensioned member portion of reduced diameter extending from an end thereof; at least one compressible outer spacer, the pre-tensioned member portion being received in the spacer, the spacer being positioned between the at least two bone anchor attachment structures; and at least one sleeve, the pre-tensioned member portion being received within the sleeve and in slidable relationship therewith, the sleeve being in engagement with the other of the at least two bone anchor attachment structures. In some embodiments, the longitudinal connecting member also includes one or more of an elastic bumper and a fixation structure. Further, the pre-tensioned member portion is fixed to the anchor member portion at an end thereof, in some embodiments.

In still another embodiment, a medical implant assembly having at least two bone attachment structures cooperating with a longitudinal connecting member is provided, the improvement wherein the longitudinal connecting member includes an anchor member portion in engagement with one of the at least two bone attachment structures, the anchor member portion having a pre-tensioned bendable core extension of reduced diameter along a length thereof, the core extension attached to and extending from the anchor member portion and having a linear and a non-linear configuration; at least one compressible outer spacer, the core extension being received in the spacer, the spacer being positioned between the at least two bone attachment structures; and at least one sleeve, the core extension being received within the sleeve and in slidable relationship therewith, the sleeve being in engagement with the other of the at least two bone attachment structures.

In another embodiment, a medical implant assembly is provided, the assembly including a longitudinal connecting member having a stiff portion secured to at least a first bone attachment structure, the stiff portion being coaxial with a less stiff core extension portion of reduced width relative to the stiff portion, the core extension being in slidable relation with at least a second end bone attachment structure; at least one solid non-slitted outer spacer positioned entirely outside of the core extension and between the at least first and second end bone attachment structures, the spacer being in slidable relation with the core extension; and at least one end fixing structure and at least one elastic bumper, both the end fixing structure and the elastic bumper being positioned entirely outside of the at least second end bone attachment structure, wherein the bumper is positioned around the core extension and between the fixing structure and the at least second end bone attachment structure, and wherein the bumper is in slidable relation with the core extension; and wherein the fixing structure is slidable on the core section, compressible against the bumper and securable to the core extension.

In a further embodiment, the core extension is in tension. In some further embodiments, the core extension is maintained in tension by axial elastic distraction from the bumper. In some further embodiments, the core extension is made of at least one of a polymer, PEEK and a non-metal. In some further embodiments, at least one sleeve is positioned around and between the core extension and the bone attachment structure, the sleeve being secured to at least the bone attachment structure. In some further embodiments, the tensioned core extension is adapted to provide resilient bending stiffness for the longitudinal connecting member while cooperating with the bone attachment structures. In some further embodiments, the end fixing structure is positioned entirely outside of the bumper. In some further embodiments, the bumper and the spacer are positioned entirely outside of the sleeve.

OBJECTS AND ADVANTAGES OF THE INVENTION

An object of the invention is to provide dynamic medical implant stabilization assemblies having longitudinal connecting members that include a pre-tensioned inner core that allows for some bending, torsion, compression and distraction of the assembly. Another object of the invention is to provide such an assembly including an elastic pre-compressed outer spacer or sleeve. A further object of the invention is to provide dynamic medical implant longitudinal connecting members that may be utilized with a variety of bone screws, hooks and other bone anchors. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged front elevational view of a dynamic fixation connecting member assembly according to the invention including an anchor member integral with an inner core, two elastic spacers, two sleeves, an elastic bumper and a crimping ring.

FIG. 2 is a cross-sectional view taken along the line 2-2 of FIG. 1.

FIG. 3 is an enlarged perspective view of the anchor member of FIG. 1.

FIG. 4 is an enlarged perspective view of one of the sleeves of FIG. 1.

FIG. 5 is an enlarged perspective view of another of the sleeves of FIG. 1.

FIG. 6 is an enlarged exploded front elevational view of the assembly of FIG. 1.

FIG. 7 is an enlarged perspective view of the crimping ring of FIG. 1.

FIG. 8 is an enlarged perspective view of the elastic bumper of FIG. 1.

FIG. 9 is an enlarged front perspective view of an elastic spacer of FIG. 1.

FIG. 10 is an enlarged rear perspective view of the elastic spacer of FIG. 9.

FIG. 11 is an enlarged front perspective view of another elastic spacer of FIG. 1.

FIG. 12 is an enlarged rear perspective view of the elastic spacer of FIG. 11.

FIG. 13 is a reduced front elevational view of the assembly of FIG. 1 shown with three cooperating bone screws.

FIG. 14 is an enlarged front elevational view of a second embodiment of a dynamic fixation connecting member assembly according to the invention including an anchor member integral with an inner core, an elastic spacer, a sleeve, an elastic bumper and a crimping ring.

FIG. 15 is a reduced exploded front elevational view of the assembly of FIG. 14.

FIG. 16 is a cross-sectional view taken along the line 16-16 of FIG. 14.

FIG. 17 is a reduced front elevational view of the assembly of FIG. 14 shown with three cooperating bone screws.

FIG. 18 is front elevational view of a third embodiment of a dynamic fixation connecting member assembly according to the invention shown with four cooperating bone screws.

FIG. 19 is a front elevational view of a fourth embodiment of a dynamic fixation connecting member assembly according to the invention with portions broken away to show the detail thereof.

FIG. 20 is a front elevational view of a fifth embodiment of a dynamic fixation connecting member assembly according to the invention with an inner threaded core shown in phantom.

FIG. 27 is an enlarged exploded front elevational view of the assembly of FIG. 25.

FIG. 29 is an enlarged side elevational view of the anchor member of FIG. 25.

FIG. 30 is an enlarged perspective view of the spacer of FIG. 25.

FIG. 31 is an enlarged side elevational view of the spacer of FIG. 25.

FIG. 38 is an enlarged front elevational view of the assembly of FIG. 25 shown with two cooperating bone screws with portions broken away to show the detail thereof.

FIG. 39 is an enlarged perspective view of a ninth embodiment of a dynamic fixation connecting member assembly according to the invention including an anchor member integral with an inner core, an elastic spacer with a trapezoidal face, a sleeve, an elastic bumper and a crimping member.

DETAILED DESCRIPTION OF THE INVENTION

Figure 24:
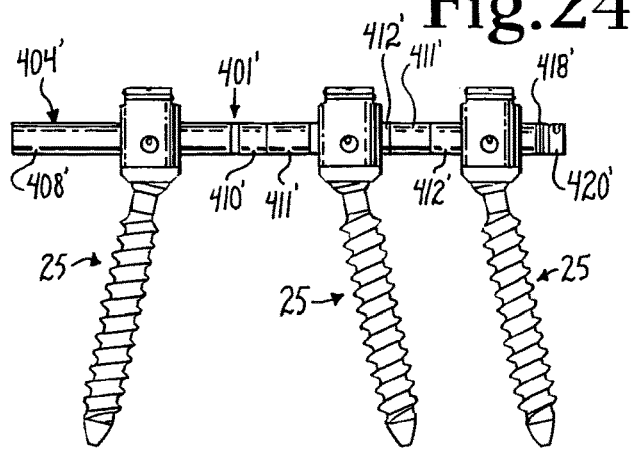
FIG. 24 is a front elevational view of a seventh embodiment of a dynamic fixation connecting member assembly according to the invention shown with three bone screws.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-13, the reference numeral 1 generally designates a non-fusion dynamic stabilization longitudinal connecting member assembly according to the present invention. The connecting member assembly 1 includes an anchor member, generally 4, having an elongate segment or inner core 6 and a bone anchor attachment portion 8; a first elastic spacer 10; a first sleeve 12; a second elastic spacer 14; a second sleeve 16; an elastic bumper 18; and a crimping ring 20; all substantially symmetrically aligned with respect to a central axis A of the anchor member 4. The elongate core 6 of the anchor member 4 is receivable within the spacer 10, the first sleeve 12, the second spacer 14, the second sleeve 16, the bumper 18 and the crimping ring 20. Thus, the axis A of the anchor member 4 is also the axis of the fully assembled assembly 1. As will be described in greater detail below, when fully assembled and fixed with all components fixed in position as shown in FIG. 1, the inner core 6 is in tension and the spacers 10 and 14 and the bumper 18 are in compression.

As illustrated in FIG. 13, the dynamic connecting member assembly 1 cooperates with at least three bone anchors, such as the polyaxial bone screws, generally 25 and cooperating closure structures 27, the assembly 1 being captured and fixed in place at the anchor portion 8, the sleeve 12 and the sleeve 16 by cooperation between the bone screws 25 and the closure structures 27. Because the anchor portion 8 and the sleeves 12 and 16 have substantially solid cylindrical surfaces, the connecting member assembly 1 may be used with a wide variety of bone screws and other bone anchors already available for cooperation with more rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, external or internal drives, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screws 25 each include a shank 30 for insertion into a vertebra (not shown), the shank 30 being pivotally attached to an open receiver or head 31. The shank 30 includes a threaded outer surface and may further include a central cannula or through-bore disposed along an axis of rotation of the shank. The through bore provides a passage through the shank interior for a length of wire or pin inserted into the vertebra prior to the insertion of the shank 30, the wire or pin providing a guide for insertion of the shank 30 into the vertebra. The receiver 31 includes a pair of spaced and generally parallel arms that form an open generally U-shaped channel therebetween that is open at distal ends of such arms. The receiver arms each include radially inward or interior surfaces that have a discontinuous guide and advancement structure mateable with cooperating structure on the closure structure 27. The guide and advancement structure may be a partial helically wound flangeform configured to mate under rotation with a similar structure on the closure structure 27 or a buttress thread, a square thread, a reverse angle thread or other thread like or non-thread like helically wound advancement structures for operably guiding under rotation and advancing the closure structure 27 downward between the receiver arms and having such a nature as to resist splaying of the receiver arms when the closure 27 is advanced between the receiver arms.

The shank 30 and the receiver 31 may be attached in a variety of ways. For example, a spline capture connection as described in U.S. Pat. No. 6,716,214, and incorporated by reference herein, may be used wherein the bone screw shank includes a capture structure mateable with a retaining structure disposed within the receiver. The retaining structure includes a partially spherical surface that is slidingly mateable with a cooperating inner surface of the receiver 31, allowing for a wide range of pivotal movement between the shank 30 and the receiver 31. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member or may include compression members or inserts that engage the bone screw shank and cooperate with the shank, the receiver and the closure structure to secure the connecting member assembly to the bone screw and/or fix the bone screw shank at a desired angle with respect to the bone screw receiver that holds the longitudinal connecting member assembly. Furthermore, although the closure structure 27 of the present invention is illustrated with the polyaxial bone screw 25 having an open receiver or head 31, it foreseen that a variety of closure structure may be used in conjunction with any type of medical implant having an open or closed head or receiver, including monoaxial bone screws, hinged bone screws, hooks and the like used in spinal surgery.

To provide a biologically active interface with the bone, the threaded shank 30 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_n(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIG. 13, the closure structure 27 can be any of a variety of different types of closure structures for use in conjunction with the present invention with suitable mating structure on the interior surface of the upstanding arms of the receiver 31. The illustrated closure structure 27 is rotatable between the spaced arms, but could be a slide-in closure structure. The illustrated closure structure 27 is substantially cylindrical and includes an outer helically wound guide and advancement structure in the form of a flange form that may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 27 downward between the receiver arms and having such a nature as to resist splaying of the arms when the closure structure 27 is advanced into the U-shaped channel formed by the arms. The illustrated closure 27 further includes an inner set screw with an internal drive in the form of an aperture utilized for assembly of the set screw and removal of the entire closure 27. It is foreseen that the closure structure 27 may alternatively include an external drive, such as a break-off head designed to allow such a head to break from a base of the closure at a preselected torque, for example, 70 to 140 inch pounds. Such a closure structure would also include a base having an internal drive to be used for closure removal.

Returning to the longitudinal connecting member assembly 1 illustrated in FIGS. 1-13, the assembly 1 is elongate, with the inner core 6 being a substantially solid, smooth and uniform cylinder or rod having an outer cylindrical surface 36 and a substantially circular cross-section. The core 6 and integral anchor attachment portion 8 may be made from metal, metal alloys or other suitable materials, including plastic polymers such as polyetheretherketone (PEEK), ultra-high-molecular weight-polyethylene (UHMWP), polyurethanes and composites, including composites containing carbon fiber. It is noted that although an anchor member 4 is illustrated in which the components 6 and 8 are integral, the core 6 and the anchor attachment portion 8 may be made from different materials, for example, the core 6 may be made out of PEEK and fixed or adhered to a bone anchor attachment portion 8 made out of titanium. The core 6 and attachment portion 8 may include a small central lumen or through-bore (not shown) extending along the central axis A. Such a lumen may be used as a passage through the entire assembly 1 interior for a length of a guide wire for aiding insertion of the assembly 1 between implanted bone screws 25 in a percutaneous or less invasive procedure.

With particular reference to FIG. 3, the anchor member 4 is substantially cylindrical along an entire length thereof along the axis A and includes at least two or more circular cross-sections along the length thereof. The illustrated member 4 includes the slender and thus more flexible core 6 of a first circular cross-section and the bone anchor attachment portion 8 that has a second circular cross-section that is larger than the core 6 cross-section and thus is more rigid than the core 6. The core 6 terminates at an end 38. Prior to final assembly, the core 6 is typically of a length greater than that shown in the drawing figures so that the core 6 may be grasped by a tool (not shown) near the end 38 and pulled along the axis A in a direction away from the anchor attachment portion 8 in order to place tension on the core 6 as will be described in greater detail below.

With particular reference to FIGS. 2-3, between the core 6 and the portion 8 is a buttress plate 40 that has a third circular cross-section that is larger than the attachment portion 8 cross-section. The buttress plate 40 is integral with and disposed between the core 6 and the portion 8. Although the illustrated anchor member 4 is substantially cylindrical, it is foreseen that the core 6, the portion 8 and the plate 40 may have other forms, including but not limited to oval, square and rectangular cross-sections as well as other curved or polygonal shapes. The bone anchor attachment portion 8 is of a length along the axis A for cooperating with at least one and up to a plurality of bone attachment members, such as the bone screws 25, hooks or other types of bone anchors. The portion 8 is substantially solid and rigid, with an outer cylindrical surface 39 that terminates at an end 41. The plate 40 includes a first substantially flat and annular face 42 facing away from the core 6 and an opposed parallel substantially flat face 44 facing toward the core 6. The faces 42 and 44 are disposed substantially perpendicular to the axis A. An outer cylindrical surface 46 extends between the faces 42 and 44. A gently sloping transition surface or flange 48 bridges between and connects the outer cylindrical surface 36 of the core 6 with the substantially flat face 44 of the buttress plate 40.

With particular reference to FIGS. 4 and 5, the sleeves 12 and 16 are each sized and shaped to be slidingly received over the core 6 along the axis A and each have a length measured along the axis A that is sufficient for the attachment of at least one bone screw 25 thereon. Similar to the anchor member 4, the sleeves 12 and 16 may be made from metal, metal alloys or other suitable materials, including plastic polymers such as polyetheretherketone (PEEK), ultra-high-molecular weight-polyethylene (UHMWP), polyurethanes and composites, including composites containing carbon fiber. The sleeves 12 and 16 may be made of the same material as the cooperating core 6, for example, the anchor member 4 and the sleeves 12 and 16 may all be made from PEEK; or, for example, the core 6 may be made from one material, such as PEEK, while the sleeves 12 and 16 may be made from another material, such as a metal (e.g. stainless steel or titanium). In order to have low or no wear debris, the sleeve 12 and 16 inner surfaces and/or cooperating core 6 outer surfaces may be coated with an ultra thin, ultra hard, ultra slick and ultra smooth coating, such as may be obtained from ion bonding techniques and/or other gas or chemical treatments.

The illustrated sleeves 12 and 16 each are substantially cylindrical, having outer cylindrical bone anchor attachment surfaces 50 and 52, respectively, that are each of substantially the same diameter as the outer surface 39 of the bone anchor attachment portion 8. Each of the sleeves 12 and 16 further include an inner cylindrical surface 54 and 56, respectively, that define a through-bore for the passage of the core 6 therethrough. The sleeve 12 includes a pair of integral, opposed end plates 58 and 60 while the sleeve 16 includes a single end plate 62. The illustrated plates 58, 60 and 62 have outer cylindrical surfaces 64, 66 and 68, respectively, that are of substantially the same diameter as the buttress plate outer cylindrical surface 46. The plates 58 and 60 terminate at outer planar and annular surfaces 70 and 72, respectively. The plate 62 terminates at an outer planar and annular surface 74. The cylindrical surface 52 of the sleeve 16 terminates at an outer planar and annular surface 76.

With reference to FIGS. 8-12, the elastic spacers 10 and 14 and the elastic bumper 18 are sized and shaped to be slidingly received over the core 6 and may be made from a variety of elastic materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacers 10 and 14 and bumper 18 inner and side surfaces may also be coated with an ultra thin, ultra hard, ultra slick and ultra smooth coating, such as may be obtained from ion bonding techniques and/or other gas or chemical treatments.

The illustrated spacers 10 and 14 advantageously cooperate with the core 6 of the anchor member 4, providing limitation and protection of movement of the core 6 located between bone screws 25. With particular reference to FIGS. 9-12, the illustrated spacers 10 and 14 are almost identical, differing only with regard to inner surfaces that define through bores for receiving the anchor member core 6. Each of the spacers 10 and 14 have an external substantially cylindrical outer surface 78 and 80, respectively, and internal surfaces 82 and 84, respectively, defining through bores. The internal surface 82 is further defined by a flared or conical outwardly extending surface 86 sized and shaped for cooperating with the surface 48 of the anchor member 4. The spacer 10 includes opposed substantially planar and annular end surfaces 88 and 89 and the spacer 14 includes opposed substantially planar and annular end surfaces 90 and 91. When cooperating with the core 6, the end surfaces 88 and 89 and 90 and 91 are substantially perpendicular to the axis A. It is foreseen that in some embodiments, the spacers 10 and 14 may be of circular, square, rectangular or other cross-section including curved or polygonal shapes. In the illustrated embodiment, both the spacers 10 and 14 further includes a compression groove 93 and 94, respectively. Spacers according to the invention may include one, none or any desired number of grooves that allow for some additional compression of the spacers 10 and 14 when pressed upon in an axial direction by the plates 40, 58, 60 and 62. The illustrated grooves 93 and 94 are substantially uniform and circular in cross-section, being formed in the respective external surfaces 78 and 80 and extending radially toward respective internal surfaces 82 and 84. The size of the internal surfaces 82 and 84 allow for some axially directed sliding movement of the respective spacers 10 and 14 with respect to the core surface 36.

The core 6 and cooperating compressible spacers 10 and 14 allows for some twist or turn, providing some relief for torsional stresses. The spacers 10 and 14 and cooperating plates 40, 58, 60 and 62 may cooperate to limit such torsional movement as well as bending movement. For example, a first set of pins may be inserted through the plates 40 and 60 and respective engaging spacer surfaces 89 and 88. A second set of pins may be inserted through the plates 58 and 62 and respective engaging spacer surfaces 91 and 90. It may be particularly advantageous to utilize pins made from tantalum, for example to provide x-ray markers, for example, when the anchor member 4, sleeves and spacers are made from radiolucent plastics. In other embodiments according to the invention, the spacers 10 and 14 and cooperating plates 40, 58, 60 and 62 may include ribs or fins for insertion into apertures located on cooperating facing surfaces to provide limits on twisting movement between such plates and spacers.

With particular reference to FIG. 8, the bumper 18 is substantially cylindrical, including an outer surface 98 and an inner surface 99 forming a substantially cylindrical through bore that opens at planar end surfaces 100 and 101 and operatively extends along the axis A. The bumper 18 further includes a compression groove 104 that is similar in form and function to the compression grooves 93 and 94 described above with respect to the spacers 10 and 14. The bumper 18 is sized and shaped to slidingly receive the core 6 through the inner surface 99. The bumper 18 is preferably made from an elastomeric material such as polyurethane. The bumper 18 operatively provides axial tension on the core 6 as will be described in greater detail below.

With particular reference to FIG. 7, the crimping ring 20 is substantially cylindrical and includes an outer surface 110 and an inner surface 112 forming a substantially cylindrical through bore that opens at planar end surfaces 114 and 116 and operatively extends along the axis A. The crimping ring 20 is sized and shaped to receive the elongate core 6 through the inner surface 112. The crimping ring 20 further includes a pair of crimp or compression grooves 120 that are pressable and deformable inwardly toward the axis A upon final tensioning of the core 6 and compression of the spacers 10 and 14 and the bumper 18 during assembly of the assembly 1. The crimping ring 20 is preferably made from a stiff, but deformable material, including metals and metal alloys.

The illustrated dynamic connecting member assembly 1 having a pre-tensioned core 6 cooperates with at least three bone anchors, such as polyaxial bone screws, generally 25 as shown in FIG. 13. In use, the three bone screws 25 are implanted into vertebrae (not shown). Each vertebra may be pre-drilled to minimize stressing the bone. Furthermore, when a cannulated bone screw shank is utilized, each vertebra will have a guide wire or pin inserted therein that is shaped for the bone screw cannula of the bone screw shank 30 and provides a guide for the placement and angle of the shank 30 with respect to the cooperating vertebra. A further tap hole may be made and the shank 30 is then driven into the vertebra by rotation of a driving tool (not shown) that engages a driving feature on or near a top portion of the shank 30. It is foreseen that both the screws 25 and the longitudinal connecting member assembly 1 may be inserted in a conventional, percutaneous or other minimally invasive surgical manner.

With particular reference to FIGS. 1, 2 and 6, the longitudinal connecting member assembly 1 is assembled to provide a pre-tensioned core 6 and pre-compressed spacers 10 and 14 and bumper 18 prior to implanting the assembly 1 in a patient. This is accomplished by first providing the anchor member 4 that has a core 6 that is longer in the axial direction A than the core 6 illustrated in the drawing figures. The spacer 10 is first loaded onto the core 6 by inserting the core 6 end 38 into the bore defined by the inner surface 82 with the face 89 directed toward the buttress plate 40. The spacer 10 is moved along the core 6 until the surface 86 contacts the surface 48. The sleeve 12 is then threaded onto the core 6 with the face 72 of the plate 60 facing the end surface 88 of the spacer 10. The core 6 is received in the bore defined by the inner cylindrical surface 54 and the sleeve 12 is moved along the core 6 until the plate surface 72 abuts the spacer surface 88. The spacer 14 is thereafter loaded onto the core 6 by inserting the core 6 end 38 into the bore defined by the inner surface 84 with the face 91 facing the toward the end plate 58 of the sleeve 12. The spacer 14 is moved along the core 6 until the surface 91 contacts the surface 70. The sleeve 16 is then threaded onto the core 6 with the face 74 of the plate 62 facing the end surface 90 of the spacer 14. The core 6 is received in the bore defined by the inner cylindrical surface 56 and the sleeve 16 is moved along the core 6 until the plate surface 74 abuts the spacer surface 90. The bumper 18 is thereafter loaded onto the core 6 by inserting the core 6 end 38 into the bore defined by the inner surface 99 with the face 101 facing the toward the surface 76 of the sleeve 16. The bumper 18 is moved along the core 6 until the surface 101 contacts the surface 76. The crimping ring 20 is thereafter loaded onto the core 6 by inserting the core 6 end 38 into the bore defined by the inner surface 112 with the face 116 facing the toward the surface 100 of the bumper 18. The crimping ring 20 is moved along the core 6 until the surface 116 contacts the surface 100. It is noted that due to the symmetrical nature of the sleeve 12, the spacer 14, the bumper 18 and the crimping ring 20, these components may be loaded onto the core 6 from either side thereof.

After the crimping ring 20 is loaded onto the core 6, manipulation tools (not shown) are used to grasp the core 6 near the end 38 and at the bone anchor attachment portion 8, placing tension on the core 6. Furthermore, the spacer 10, the sleeve 12, the spacer 14, the sleeve 16, the bumper 18 and the crimping ring 20 are moved toward the buttress plate 40 and into contact with one another. Axial compressive force may also be placed on the components loaded on the core 6, followed by deforming the crimping ring at the crimp grooves 120 and against the core 6. When the manipulation tools are released, the crimping ring 20, now firmly and fixedly attached to the core 6 holds the spacers 10 and 14 and the bumper 18 in compression and the spacers and bumper place axial tension forces on the core 6, resulting in a dynamic relationship between the core 6 and the spacers 10, 14 and the bumper 18. The tension on the core 6 is advantageously balanced and uniform as the spacers 10 and 16 are slidable with respect to the core 6, but also are limited by the buttress plate of the anchor member 4 and end plates of the sleeves 12 and 16. Furthermore, the bumper 18 that is compressed between the sleeve surface 76 and the crimping ring surface 116 is also slidable with respect to the core 206. The spacers 10 and 14 and the bumper 18 place a distractive force on the core 6 along the axis A and between the buttress plate 40 and the crimping ring 20, but also are movable with respect to the core 6, thus being able to respond to jolting and other body movements and thereafter spring back into an originally set location. The sleeves 12 and 16 that may compress slightly, but are more rigid than the spacers 10 and 14, keep the spacers 10 and 14 in an approximate desired axially spaced relation. However, the spacers 10 and 14 also advantageously slide along the core 6 in response to outside forces. The core 6 is then trimmed to be approximately flush with the end surface 114 of the crimping ring 20.

With reference to FIG. 13, the pre-loaded connecting member assembly 1 is eventually positioned in an open, percutaneous or other less invasive manner in cooperation with the at least three bone screws 25 with the spacers 10 and 14 being disposed between and spaced from the bone screws 25 and with the portion 8 and sleeves 12 and 16 each being located within a U-shaped channel of a cooperating bone screw receiver 31. Once a desired position is attained, a closure structure 27 is then inserted into and advanced between the arms of each of the bone screw receivers 31 until appropriately tightened.

The assembly 1 is thus substantially dynamically loaded and oriented relative to the cooperating vertebra, providing relief (e.g., shock absorption) and protected movement with respect to flexion, extension, distraction and compressive forces placed on the assembly 1 and the three connected bone screws 25. The slender core 6 allows for some twisting or turning, providing some relief for torsional stresses. Furthermore, the compressed spacers 10 and 14 place some limits on torsional movement as well as bending movement, to provide spinal support. The pre-loaded core 6 (in tension) and spacers 10, 14 and bumper 18 (in compression) allow for compression and some extension of the assembly 1 located between the two bone screws 25, e.g., shock absorption.

If removal of the assembly 1 from any of the bone screw assemblies 25 is necessary, or if it is desired to release the assembly 1 at a particular location, disassembly is accomplished by using the driving tool (not shown) with a driving formation cooperating with the closure structure 27 internal drive or cooperating set screw internal drive to rotate and remove the closure structure 27 from the receiver 31. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the portion 8 and the sleeves 12 and 16, utilizing the same receivers 31 and the same or similar closure structures 27. Alternatively, if less support is eventually required, a less rigid, more flexible assembly, for example, an assembly 1 having components made of a more flexible material, but with the same diameter sleeves as the assembly 1, may replace the assembly 1, also utilizing the same bone screws 25.

With reference to FIGS. 14-17, an alternative embodiment of a dynamic longitudinal connecting member, generally 201, includes an anchor member, generally 204, having an elongate segment or inner core 206 and a bone anchor attachment portion 208; an elastic spacer 210; a sleeve 216; an elastic bumper 218; and a crimping ring 220; all substantially symmetrically aligned with respect to a central axis B of the anchor member 204. The elongate core 206 of the anchor member 204 is receivable within the spacer 210, the sleeve 216, the bumper 218 and the crimping ring 220. Thus, the axis B of the anchor member 204 is also the axis of the fully assembled assembly 201. When fully assembled and fixed with all components fixed in position as shown in FIG. 14, the inner core 206 is in tension and the spacer 210 and the bumper 218 are in compression.

In the illustrated embodiment, the anchor member 204 is substantially similar to the anchor member 4 previously described herein with respect to the assembly 1. Therefore, the member 204 includes the core 206, the bone anchor attachment portion 208 and an integral buttress plate 240 identical or substantially similar in size and shape to the respective core 6, attachment portion 8 and buttress plate 40 of the anchor member 4 previously described herein. The member 204 differs from the member 4 only in the length of the bone anchor attachment portion 208. The portion 208 is longer than the similar portion 8 of the member 4 such that at least two bone screws 25 are attachable to the portion 208 as illustrated in FIG. 17 while only one bone screw 25 is attached to the portion 8 of the assembly 1. The spacer 210 is identical or substantially similar to the spacer 10 illustrated in FIGS. 11 and 12 and previously described herein. The sleeve 216 is identical or substantially similar to the sleeve 16 illustrated in FIG. 4 and previously described herein, having an outer cylindrical surface 252, an inner cylindrical surface 256 defining a through bore and an end plate 262 identical or substantially similar to the respective outer cylindrical surface 52, inner cylindrical surface 56 and end plate 62 of the sleeve 16 previously described herein. The bumper 218 and the crimping ring 220 are identical or substantially similar to the respective bumper 18 and the crimping ring 20 previously described herein with respect to the assembly 1.

The assembly 201 is assembled in a manner substantially similar to the manner of assembly previously described herein with respect to the assembly 1, the assembly 201 however, does not include a second spacer or second sleeve. Therefore, the core 206 is first received within a through bore of the spacer 210, then within the inner cylindrical surface 256 of the sleeve 216, followed by an inner through bore of the bumper 218 and then an inner through bore of the crimping ring 220. Similar to what has been described previously with respect to the assembly 1, the core 206 is initially of a longer length measured along the axis B than is shown in the drawing figures, allowing for a manipulation tool to grasp the core 206 near an end thereof that extends through the crimping ring bore. The core 206 is tensioned and/or the spacer 210 and bumper 220 are compressed, followed by deformation of the crimping ring 220 against the core 206. The core 206 is then trimmed substantially flush to the crimping ring 220. The assembly is now in dynamic relationship with the core 206 being in tension while the spacer 210 that is slidable with respect to the core 206 is compressed between the plates 240 and 262 and the bumper 218 that is also slidable with respect to the core 206 is compressed between the sleeve 216 and the crimping ring 220; the spacer 210 and the bumper 218 placing a distractive force on the core 206 along the axis B and between the buttress plate 240 and the crimping ring 220. The assembly 201 may then be implanted, cooperating with three bone screws 25 as illustrated in FIG. 17 and as previously described herein with respect to the assembly 1. Unlike the assembly 1 illustrated in FIG. 13 that provides for a more dynamic and flexible connection between all three illustrated bone screws 25, the assembly 201 provides for dynamic stabilization between first and second bone screws 25 and a more rigid connection between the second bone screw 25 and a third bone screw 25 as both the second and third bone screws are attached to the rigid attachment portion 208.

With reference to FIG. 18, a third embodiment of a dynamic longitudinal connecting member assembly, generally 301 is illustrated. The assembly 301 includes an anchor member 304 having an inner core 306 and a bone anchor attachment portion 308; a spacer 310, a sleeve 316, a bumper 318 and a crimping ring 320. The illustrated spacer 310, sleeve 316, bumper 318 and crimping ring 320 are identical to the spacer 210, sleeve 216, bumper 218 and crimping ring 220 previously described herein with respect to the assembly 201. The anchor member 304 is identical to the anchor member 204 with the exception that the bone anchor attachment portion 308 is of a length to receive three bone screw receivers 31 therealong while the portion 208 is sized to receive two bone screw receivers 31. It is foreseen that longitudinal connecting member assemblies according to the invention may be of a variety of lengths for cooperation with a plurality of bone screws 25, either along a rigid end portion, such as the portion 308 shown in FIG. 18, or along dynamic portions that include one or more spacers and one or more sleeves, such as the sleeves 12 and 16 for attachment to bone screws 25 or other bone anchors. It is foreseen that such sleeves may also be a variety of lengths for attachment to one or more bone anchors along a length of the individual sleeve.

With reference to FIGS. 19 and 20, fourth and fifth embodiments of a dynamic longitudinal connecting member assembly of the invention are illustrated. With reference to FIG. 19, an assembly 1' is illustrated that is substantially similar to the assembly 1 previously described herein with an anchor member, generally 4', having an inner core extension 6' fixed to a bone anchor attachment portion 8'; spacers 10' and 14'; sleeves 12' and 16'; a bumper 18' and a crimping ring 20', all aligned along an axis A'. The illustrated spacers 10' and 14', sleeves 12' and 16', bumper 18' and crimping ring 20' are identical or substantially similar to the respective spacers 10 and 14, sleeves 12 and 16, bumper 18 and crimping ring 20 of the assembly 1. The embodiment 1' differs from the assembly 1 only in how the core extension 6' is fixed to the bone anchor attachment portion 8'. In the assembly 1' the attachment portion 8' includes a threaded aperture T and the core extension 6' includes an outer threaded portion 36' that mates with the threaded aperture T, fixing the core extension 6' to the portion 8' upon rotation of the core extension 6' about the axis A' within the aperture T.

With reference to FIG. 20, another embodiment of the invention, an assembly 201', is shown that is substantially similar to the assembly 201 illustrated in FIGS. 14-17. The assembly 201' includes an anchor member, generally 204', having an inner core extension 206' fixed to a bone anchor attachment portion 208'; a spacer 210'; a sleeve 216'; a bumper 218' and a crimping ring 220', all aligned along an axis B'. The illustrated spacer 210', sleeve 216', bumper 218' and crimping ring 220' are identical or substantially similar to the respective spacer 210, sleeve 216, bumper 218 and crimping ring 220 of the assembly 201. The embodiment 201' differs from the assembly 201 only in how the core extension 206' is fixed to the bone anchor attachment portion 208'. In the assembly 201' the attachment portion 208' includes a threaded aperture T' and the core extension 206' includes an outer threaded portion 236' that mates with the threaded aperture T', fixing the core extension 206' to the portion 208' upon rotation of the core extension 206' about the axis B' within the aperture T'. It is noted that the aperture T shown in FIG. 19 extends completely through the portion 8' while the aperture T' shown in FIG. 20 extends substantially into the portion 208' along the axis B', but does not extend therethrough.

Figure 21:
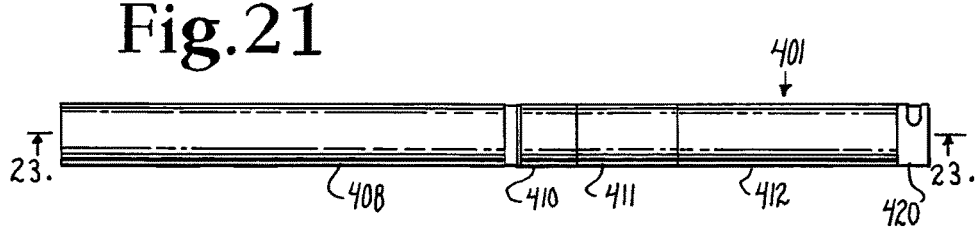
FIG. 21 is a front elevational view of a sixth embodiment of a dynamic fixation connecting member assembly according to the invention.
Figure 22:
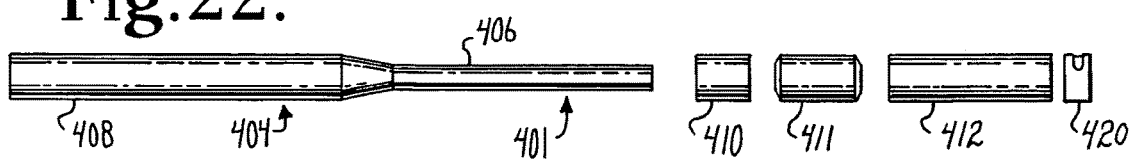
FIG. 22 is a reduced exploded front elevational view of the connecting member of FIG. 21.
Figure 23:
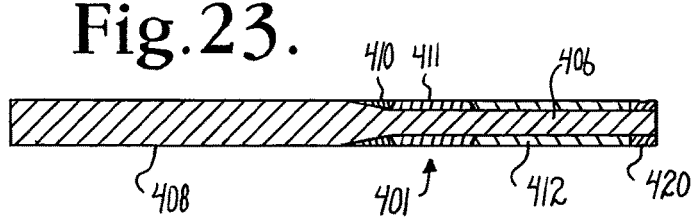
FIG. 23 is a reduced cross-sectional view taken along the line 23-23 of FIG. 21.

With reference to FIGS. 21-23, another embodiment of a connecting member according to the invention, an assembly 401 is shown that includes the same or similar components to the assemblies 1 and 201, for example, previously described herein. However, the components are sized such that the resulting assembly 401 has a constant outer diameter along an entire length thereof. Thus, the assembly 401 generally designates a non-fusion dynamic stabilization longitudinal connecting member assembly according to the present invention having an anchor member, generally 404, that includes an elongate segment or inner core 406 integral with or otherwise fixed to a bone anchor attachment portion 408; an end spacer or stop 410; a second elastic spacer 411; a rigid sleeve 412; and a crimping ring 420; all substantially symmetrically aligned with respect to a central axis of the anchor member 404. The elongate core 406 of the anchor member 404 is receivable within the spacers 410 and 411, the sleeve 412 and the crimping ring 420. Thus, the central axis of the anchor member 404 is also the axis of the fully assembled assembly 401. Although not shown, the core 406 may be made of a slightly longer length and an elastic bumper, similar to the bumper 18 of the assembly 1 (but of a different inner diameter, such as the bumper 418' shown in FIG. 24) may be placed between the sleeve 412 and the crimping ring 420. The core 406, anchor attachment portion 408, spacers 410 and 411, sleeve 412 and crimping ring 420 are substantially similar in form and function to the respective core 6, anchor attachment portion 8, spacer 10, sleeve 12 and crimping ring 20 of the assembly 1. In the illustrated embodiment 401, the two spacers 410 and 411 may be made out of the same or different materials. For example, it may be desirable to make the spacer 410 of a more rigid material than the spacer 411 to provide more of a stop or barrier between the anchor attachment portion 408 and the spacer 411 in light of the reduced size of the components of the assembly 401 as compared to the assembly 1 and the fact that the assembly 401 does not include a buttress plate such as the buttress plate 40 of the assembly 1. It is foreseen that in certain embodiments of the invention, the two spacers 410 and 411 may be replaced by a single spacer. Furthermore, rather than a gradual decrease in diameter from the portion 408 to the core 406 shown in the drawings, the anchor attachment portion 408 and the core 406 may be configured in a more abrupt or stepped manner, forming a small stop or abutment surface disposed perpendicular to the central axis of the anchor member 404.

Similar to the assembly 1, the assembly 404, when fully assembled, has the inner core 406 in tension and at least the spacer 411 in compression, with the ring 420 crimped against the core 406. The dynamic connecting member assembly 401 cooperates with at least two bone anchors (not shown), such as the anchors 25, the anchors being attached to the portion 408 and the rigid sleeve 412.

With reference to FIG. 24, another embodiment of a connecting member according to the invention, an assembly 401', is shown that is substantially similar to the assembly 401. The assembly 401' differs from the assembly 401 only that the assembly 401' includes a bumper 418', a pair of spacers 411' identical or substantially similar to the spacer 411 and a pair of rigid sleeves 412' identical or substantially similar to the sleeve 412, allowing for a bone screw 25 to be attached to each sleeve 412' as well as to the anchor portion 408', for a total of at least three bone screws 25. One spacer 411' is disposed between each bone screw 25. Thus, the assembly 401' includes an anchor member 404' that includes an elongate segment or inner core (not shown, but substantially similar to the core 406 shown in FIG. 22) and an integral bone anchor attachment portion 408'; an end spacer or stop 410'; a pair of elastic spacers 411'; a pair of rigid sleeves 412'; and a crimping ring 420'; all substantially symmetrically aligned with respect to a central axis of the anchor member 404'. The elongate core of the anchor member 404' is receivable within the end spacer 410', the spacers 411', the sleeves 412' and the crimping ring 420' as well as the elastic bumper 418' that is similar in form and function to the bumper 18 of the assembly 1. Thus, the anchor member 404', spacers 411, sleeve 412, bumper 418' and crimping ring 420 are substantially similar in form and function to the respective anchor member 4, spacer 10, sleeve 12, bumper 18 and crimping ring 20 of the assembly 1. Similar to the assembly 401, the assembly 401' end spacer or stop 410' may be elastic like the spacers 411' or may be made of a more rigid material in order to function in a manner similar to the buttress plate 40 of the assembly 1.

Figure 25:
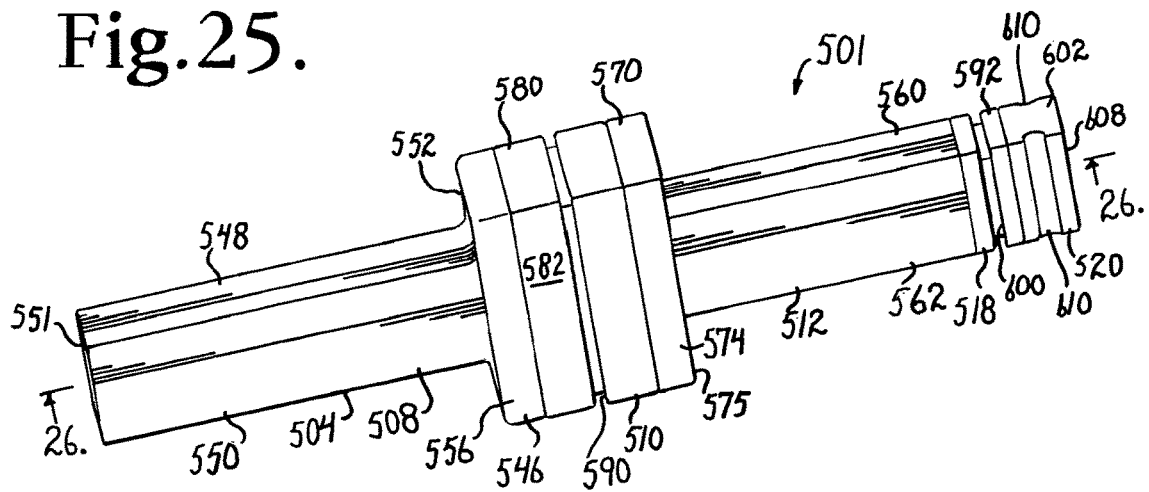
FIG. 25 is an enlarged perspective view of an eighth embodiment of a dynamic fixation connecting member assembly according to the invention including an anchor member integral with an inner core, an elastic spacer, a sleeve, an elastic bumper and a crimping member.

With reference to FIGS. 25-38, the reference numeral 501 generally designates another embodiment of a non-fusion dynamic stabilization longitudinal connecting member assembly according to the present invention. The connecting member assembly 501 includes an anchor member, generally 504, having an elongate segment or inner core or core extension 506 and a bone anchor attachment portion 508; an elastic spacer 510; a sleeve 512; an elastic bumper 518; and a crimping member 520; all substantially symmetrically aligned with respect to a central axis AA of the anchor member 504. The elongate core 506 of the anchor member 504 is receivable within the spacer 510, the sleeve 512, the bumper 518 and the crimping member 520. Thus, the axis AA of the anchor member 504 is also a central axis of the fully assembled assembly 501. As will be described in greater detail below, when fully assembled and fixed with all components fixed in position as shown in FIG. 25, the inner core 506 is in tension and the spacer 510 and the bumper 518 are in compression.

As illustrated in FIG. 38, the dynamic connecting member assembly 501 cooperates with at least two bone anchors, such as the polyaxial bone screws, generally 525 and cooperating closure structures 527, the assembly 501 being captured and fixed in place at the anchor portion 508 and the sleeve 512 by cooperation between the bone screws 525 and the closure structures 527. All of the embodiments according to the invention illustrated in FIGS. 25-52 are shown with the same bone screws 525 and cooperating closure structures 527, however, as more fully discussed below, a wide variety of bone anchors may be used with connecting members according to the invention. For example, because the anchor portion 508 and the sleeve 512 of the assembly 501 have substantially solid and planar surfaces, the connecting member assembly 501 may be used with a wide variety of bone screws and other bone anchors that closely receive the planar surfaces of the assembly 501, including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, external or internal drives, break-off tops and inner set screws. The bone anchors, closure structures and the connecting member assembly 501 are then operably incorporated in an overall spinal implant system for correcting degenerative conditions, deformities, injuries, or defects to the spinal column of a patient.

The illustrated polyaxial bone screws 525 each include a shank 530 for insertion into a vertebra (not shown), the shank 530 being pivotally attached to an open receiver or head 531. The shank 530 includes a threaded outer surface and may further include a central cannula or through-bore disposed along an axis of rotation of the shank. The through bore provides a passage through the shank interior for a length of wire or pin inserted into the vertebra prior to the insertion of the shank 530, the wire or pin providing a guide for insertion of the shank 530 into the vertebra. The receiver 531 includes a pair of spaced and generally parallel arms that form an open squared off U-shaped channel therebetween that is open at distal ends of such arms. The receiver arms each include radially inward or interior surfaces that have a discontinuous guide and advancement structure mateable with cooperating structure on the closure structure 527. The guide and advancement structure may be a partial helically wound flangeform configured to mate under rotation with a similar structure on the closure structure 527 or a buttress thread, a square thread, a reverse angle thread or other thread like or non-thread like helically wound advancement structures for operably guiding under rotation and advancing the closure structure 527 downward between the receiver arms and having such a nature as to resist splaying of the receiver arms when the closure 527 is advanced between the receiver arms.

The shank 530 and the receiver 531 may be attached in a variety of ways. For example, a threaded capture connection as described in U.S. Patent Pub. No. 2007/0055244, and incorporated by reference herein, may be used wherein the bone screw shank includes an outer helical thread mateable with an inner helical thread of a retaining structure disposed within the receiver. The shank 530 of the illustrated bone screw 525 is top loaded into the receiver 531 and includes an upper portion 536 that has a partially spherical surface that is slidingly mateable with a cooperating inner surface of the receiver 531, allowing for a wide range of pivotal movement between the shank 530 and the receiver 531. Top or bottom loaded polyaxial bone screws for use with the assembly 501 may include other types of capture connections, including but not limited to, other threadably connected, spline connected, or cam connected shank upper portions mateable with a retainer structure or ring that is in turn slidingly mateable with the inner surface of the receiver 531, frictional connections utilizing frusto-conical or polyhedral capture structures, and other types of integral top or downloadable shanks. Also, as indicated above, polyaxial and other bone screws for use with connecting members of the invention may have bone screw shanks that directly engage the elongate connecting member or, as illustrated, include at least one compression member, such as the lower insert 538 that includes a partially spherical base that engages the substantially spherical upper portion of the bone screw shank 536 and also engages the bone anchor attachment portion 508 or the sleeve 512 to securely hold the connecting member assembly 501 within the receiver 531 and/or cooperate with the closure structure 527 to fix the bone screw shank 530 at a desired angle with respect to the bone screw receiver 531. As illustrated in FIG. 38 and also shown in FIG. 48, the insert 538 includes spaced parallel walls disposed perpendicular to a bottom seating surface for closely holding the flat surfaced anchor attachment portion 508 or the flat surfaced sleeve 512 at a location slightly spaced from the squared off opening of the receiver 531.

Although the closure structure 527 for use with the assembly 501 of the present invention is illustrated with the polyaxial bone screw 525 having an open receiver or head 531, it foreseen that a variety of closure structures may be used in conjunction with any type of medical implant having an open or closed head or receiver, including monoaxial bone screws, hinged bone screws, hooks and the like used in spinal surgery.

To provide a biologically active interface with the bone, the threaded shank 530 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With further reference to FIG. 38, the closure structure 527 can be any of a variety of different types of closure structures for use in conjunction with the present invention with suitable mating structure on the interior surface of the upstanding arms of the receiver 531. The illustrated closure structure 527 is rotatable between the spaced arms, but it is foreseen that it could be a slide-in closure structure. The illustrated closure structure 527 is substantially cylindrical and includes an outer helically wound guide and advancement structure in the form of a flange form that may take a variety of forms, including those described in Applicant's U.S. Pat. No. 6,726,689, the disclosure of which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 527 downward between the receiver arms and having such a nature as to resist splaying of the arms when the closure structure 527 is advanced into the squared off U-shaped channel formed by the arms. The closure 527 may further include an inner set screw with an internal drive in the form of an aperture utilized for assembly of the set screw and removal of the entire closure 527. It is foreseen that the closure structure may alternatively include a non-helically wound locking or cam structure that may also include a flanged lip. It is also foreseen that the closure structure 527 may alternatively include an external drive, such as a break-off head designed to allow such a head to break from a base of the closure at a preselected torque, for example, 70 to 140 inch pounds. Such a closure structure would also include a base having an internal drive to be used for closure removal. In the illustrated embodiments, the closure 527 has a planar bottom surface that engages the insert 538 as well as the bone anchor portion 508 or the sleeve 512 for consistent secure locking of the polyaxial screw mechanism, the insert 538 pressing against the shank upper portion 536 that in turn presses against an inner surface of the receiver 531. It is also foreseen that the closure structure may have a roughened or point and rim structure to aid in frictionally engaging the longitudinal connecting member.

Returning to the longitudinal connecting member assembly 501 illustrated in FIGS. 25-38, the assembly 501 is elongate, with the inner core 506 being a substantially solid, smooth and uniform bar of substantially square or rectangular cross-section. The core 506 may have a variety of cross-sectional geometries including polygonal and curvate. It is preferred that the cross-section be non-circular. However, a curvate cross-section, such as an oval or elliptical shape is acceptable. As will be described in greater detail below, the non-circular shape of the core 506 advantageously provides for torsion control of the assembly whereas a similar assembly made with a core of a circular cross section may tend to slip or rotate with respect to the other components of the assembly 501 when the assembly 501 is placed under torsional forces. Such a connecting member may require further structure in the form of pegs, pins or adhesives to more firmly connect an anchor member (similar to the anchor 504 but with circular cross-section) with an outer spacer (similar to the spacer 510 but with circular cross-section), for example.

The anchor attachment portion 508 may be made from metal, metal alloys or other suitable materials, including plastic polymers such as polyetheretherketone (PEEK), ultra-high-molecular weight-polyethylene (UHMWP), polyurethanes and composites, including composites containing carbon fiber. It is noted that although an anchor member 504 is illustrated in which the components 506 and 508 are integral, the core extension 506 and the anchor attachment portion 508 may be made from different materials, for example, the core extension 506 may be made out of PEEK and fixed or adhered to a bone anchor attachment portion 508 made out of titanium. The core 506 and attachment portion 508 each include a small central lumen or through-bore 540 extending along the central axis AA. The lumen 540 may be used as a passage through the entire assembly 501 interior for a length of a guide wire for aiding insertion of the assembly 501 between implanted bone screws 525 in a percutaneous or less invasive procedure.

Figure 28:
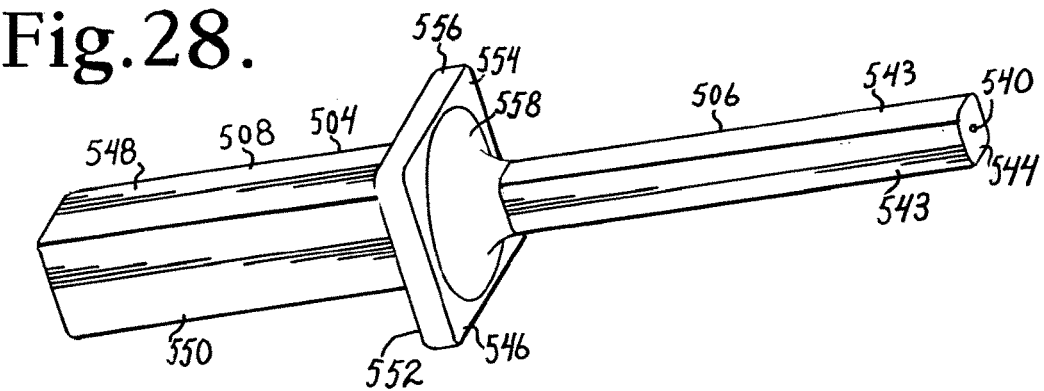
FIG. 28 is an enlarged perspective view of the anchor member of FIG. 25.

With particular reference to FIGS. 27-29, the anchor member 504 is substantially bar-shaped along an entire length thereof along the axis AA and includes at least two or more rectangular cross-sections along the length thereof. The illustrated member 504 includes the slender and thus more flexible core 506 of a first rectangular cross-section that is illustrated in the drawings as having a square cross-section with four outer planar surfaces 543. The core 506 terminates at an end 544. Prior to final assembly, the core 506 is typically of a length greater than that shown in the drawing figures so that the core 6 may be grasped by a tool (not shown) near the end 544 and pulled along the axis AA in a direction away from the anchor attachment portion 508 in order to place tension on the core 506. Alternatively, the core 506 may be grasped by a tool near the end 544 during compression of the spacer 510 and/or bumper 518 and crimping of the member 520. As will be described in greater detail below, after removal of the tools, the spacer 510 and bumper 518 expand along the axis AA, placing the core extension 506 in tension.

The bone anchor attachment portion 508 that is integral with the core extension 506 has a second rectangular cross-section that is larger than the core 506 cross-section and thus the portion 508 is more rigid than the core 506. Also with reference to FIGS. 25-29, between the core 506 and the portion 508 is a buttress plate 546 that has a rectangular cross-section that is larger than the cross-section of the attachment portion 508. The buttress plate 546 is integral with and disposed between the core 506 and the portion 508. Although the illustrated anchor member 504 is substantially rectangular, it is foreseen that the core 506, the portion 508 and the plate 546 may have other forms, including but not limited to oval and square cross-sections as well as other curved or polygonal shapes. The bone anchor attachment portion 508 is of a length along the axis AA for cooperating with at least one and up to a plurality of bone attachment members, such as the bone screws 525, hooks or other types of bone anchors. The portion 508 is substantially solid and rigid, with opposed planar surfaces 548 and perpendicular cooperating opposed planar surfaces 550. The surfaces 548 and 550 terminate at an end 551. In the illustrated embodiment, a distance between the surfaces 548 is slightly greater than a distance between the surfaces 550. This is advantageous in situations wherein a relatively stiff bar 508 is desired but space considerations such as vertebrae and tooling placement require a more slender elongate connector.

The buttress plate 546 includes a first substantially flat and annular face 552 facing away from the core 506 and an opposed parallel substantially flat face 554 facing toward the core 506. The faces 552 and 554 are disposed substantially perpendicular to the axis AA. An outer surface 556 of rectangular cross-section extends between the faces 552 and 554. A gently sloping transition surface or flange 558 bridges between and connects the surfaces 543 of the core 506 with the substantially flat face 554 of the buttress plate 546.

Figure 26:
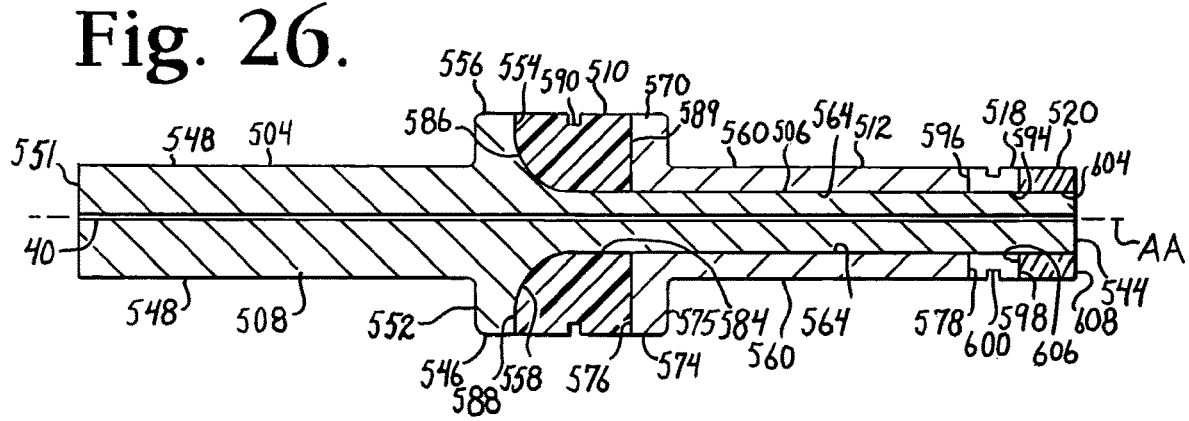
FIG. 26 is a cross-sectional view taken along the line 26-26 of FIG. 25.
Figure 32:
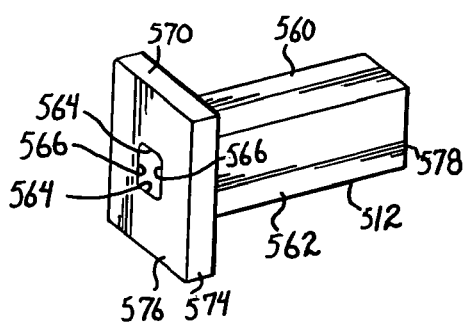
FIG. 32 is an enlarged perspective view of the sleeve of FIG. 25.
Figure 33:
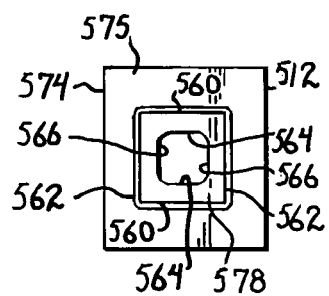
FIG. 33 is an enlarged side elevational view of the sleeve of FIG. 25.
Figure 34:
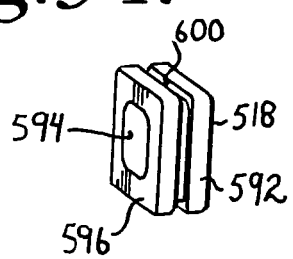
FIG. 34 is an enlarged perspective view of the elastic bumper of FIG. 25.
Figure 35:
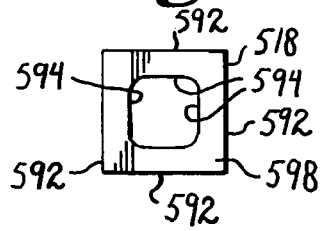
FIG. 35 is an enlarged side elevational view of the elastic bumper of FIG. 25.
Figure 36:
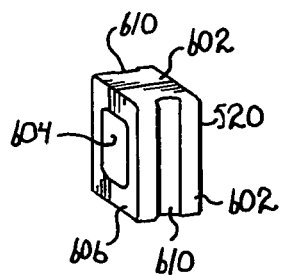
FIG. 36 is an enlarged perspective view of the crimping member of FIG. 25.
Figure 37:
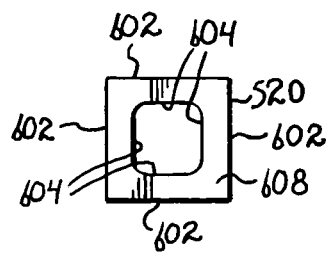
FIG. 37 is an enlarged side elevational view of the crimping member of FIG. 25.
Figure 40:
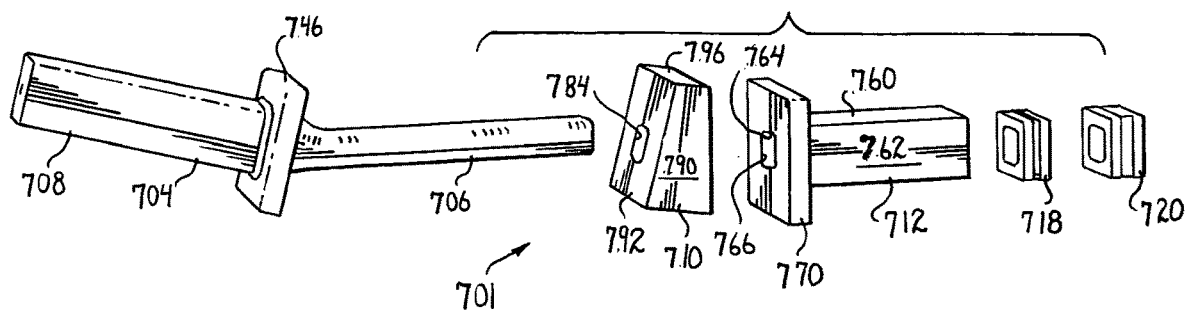
FIG. 40 is a reduced exploded perspective view of the assembly of FIG. 39.
Figure 41:
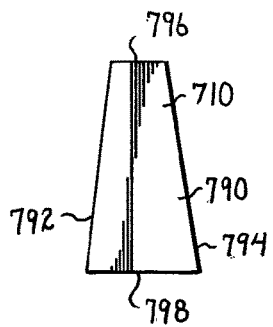
FIG. 41 is an enlarged front elevational view of the elastic spacer of FIG. 39.
Figure 42:
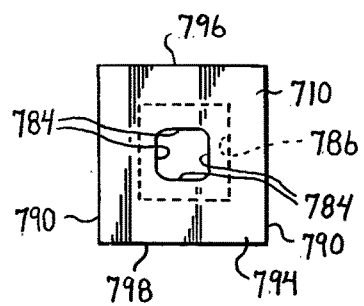
FIG. 42 is an enlarged side elevational view of the elastic spacer of FIG. 39.

With particular reference to FIGS. 26, 32 and 33, the sleeve 512 is sized and shaped to be slidingly received over the core 506 along the axis AA and has a length measured along the axis AA that is sufficient for the attachment of at least one bone screw 525 thereon. Similar to the anchor member 504, the sleeve 512 may be made from metal, metal alloys or other suitable materials, including plastic polymers such as polyetheretherketone (PEEK), ultra-high-molecular weight-polyethylene (UHMWP), polyurethanes and composites, including composites containing carbon fiber. The sleeve 512 may be made of the same material as the cooperating core 506, for example, the anchor member 504 and the sleeve 512 may be made from PEEK; or, for example, the core 506 may be made from one material, such as PEEK, while the sleeve 512 may be made from another material, such as a metal (e.g. stainless steel or titanium). In order to have low or no wear debris, the sleeve 512 inner surfaces and/or cooperating core 506 outer surfaces may be coated with an ultra thin, ultra hard, ultra slick and ultra smooth coating, such as may be obtained from ion bonding techniques and/or other gas or chemical treatments.

The illustrated sleeve 512 has a rectangular cross-section taken perpendicular to the axis AA, having outer opposed planar anchor attachment surfaces 560 and cooperating perpendicular opposed planar attachment surfaces 562. The illustrated sleeve 512 rectangular cross-section is identical or substantially similar to the rectangular cross-section formed by the surfaces 548 and 550 of the bone anchor attachment portion 508. The sleeve 512 further includes inner opposed planar surfaces 564 and cooperating perpendicular opposed planar surfaces 566 that define a through-bore for the passage of the core 506 therethrough. In the illustrated embodiment, the surfaces 564 and 566 are of substantially the same width (measured perpendicular to the axis AA) for being closely slidingly mateable with the surfaces 543 of the core 506. The sleeve 512 further includes a plate 570 at an end thereof. The illustrated end plate 570 has a rectangular cross-section perpendicular to the axis AA partially defined by outer planar surfaces 574. The surfaces 574 are sized and shaped to be identical or substantially similar to the surfaces 556 of the plate 546 of the anchor member 504. The plate 570 has a planar surface 575 perpendicular to the axis AA and an opposed terminal planar surface 576. The surfaces 560 and 562 terminate at an outer planar surface 578.

With reference to FIGS. 25-27, the elastic spacer 510 and the elastic bumper 518 are sized and shaped to be slidingly received over the core 506 and may be made from a variety of elastic materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacer 510 and the bumper 518 inner and side surfaces may also be coated with an ultra thin, ultra hard, ultra slick and ultra smooth coating, such as may be obtained from ion bonding techniques and/or other gas or chemical treatments.

The illustrated spacer 510 advantageously closely slidingly mates and cooperates with the core 506 of the anchor member 504, providing limitation and protection of axial movement and torsional control of the core 506 located between bone screws 525. With particular reference to FIGS. 26, 30 and 31, the illustrated spacer 510 has a pair of opposed planar outer surface 580 and perpendicular opposed planar cooperating surfaces 582. The surfaces 580 and 582 have an outer cross-section similar or identical in size to the plates 546 and 570. The spacer 510 also includes inner surfaces 584 of substantially the same width forming a lumen or through bore of substantially rectangular cross-section with respect to the axis AA. In the illustrated embodiment, the cross-section is substantially square and slightly larger than the substantially square cross-section of the core 506. The internal surfaces 584 are further defined by a flared outwardly extending surface 586 sized and shaped for cooperating with the surface 558 of the anchor member 504. The spacer 510 includes opposed substantially planar end surfaces 588 and 589. The flared surface 586 terminates at the end surface 588. When cooperating with the core 506, the end surfaces 588 and 589 are substantially perpendicular to the axis AA. It is foreseen that in some embodiments, the spacer 510 may be of circular, square, or other outer cross-sectional shapes including curved or polygonal shapes. In the illustrated embodiment, the spacer 510 further includes a compression groove 590. Spacers according to the invention may include one, none or any desired number of grooves 590 that allow for some additional compression of the spacer 510 when pressed upon in an axial direction by the plates 546 and 570. The illustrated groove 590 is substantially uniform and formed in the external surfaces 580 and 582 and extending inwardly toward the internal surfaces 584. The size of the internal surfaces 584 allow for some axially directed sliding movement of the spacer 510 with respect to the core surfaces 543 but limits any rotation of the spacer 510 about the axis AA and thus limits twisting movements between the anchor 504, the sleeve 512 and the spacer 510.

With particular reference to FIGS. 25-27 and 34-35, the illustrated bumper 518 is substantially square in cross-section in an operational direction perpendicular to the axis AA. The bumper 518 includes outer planar surfaces 592 and an inner bore also of substantially square cross-section with respect to the axis AA, the bore formed by inner planar surfaces 594 sized and shaped to be slightly larger than the surfaces 543 defining the core 506. The surfaces 592 and 594 terminate at planar end surfaces 596 and 598 that are operatively perpendicular to the axis AA. The bumper 518 further includes a compression groove 600 that is similar in form and function to the compression groove 590 described previously herein with respect to the spacer 510. The bumper 518 is sized and shaped to slidingly receive the core 506 through the inner surface 594. The bumper 518 is preferably made from an elastomeric material such as polyurethane. The bumper 518 operatively provides axial tension on the core 506 as will be described in greater detail below.

With particular reference to FIGS. 25-27 and 36-37, the crimping member 520 is substantially square in cross-section taken in a direction perpendicular to the axis AA and includes four substantially planar outer surfaces 602. Four planar inner surfaces 604 form a through bore also of substantially square cross-section, sized and shaped to closely slidingly receive the planar surfaces 543 of the core 506 along the axis AA. The surfaces 602 and 604 terminate at opposed planar end surfaces 606 and 608. The crimping member 520 further includes a pair of opposed crimp or compression grooves 610 that are pressable and deformable inwardly toward the axis AA upon final tensioning of the core 506 and/or compression of the spacer 510 and the bumper 518 during assembly of the assembly 501. The crimping member 520 is preferably made from a stiff, but deformable material, including, but not limited to, metals and metal alloys.

The illustrated dynamic connecting member assembly 501 having a pre-tensioned core extension 506 cooperates with at least two bone anchors, such as the polyaxial bone screws, generally 525 as shown in FIG. 38. In use, the bone screws 525 are implanted into vertebrae (not shown). Each vertebra may be pre-drilled to minimize stressing the bone. Furthermore, when a cannulated bone screw shank is utilized, each vertebra will have a guide wire or pin inserted therein that is shaped for the bone screw cannula of the bone screw shank 530 and provides a guide for the placement and angle of the shank 530 with respect to the cooperating vertebra. A further tap hole may be made and the shank 530 is then driven into the vertebra by rotation of a driving tool (not shown) that engages a driving feature on or near a top portion of the shank 530. It is foreseen that both the screws 525 and the longitudinal connecting member assembly 501 may be inserted in a conventional, percutaneous or other minimally invasive surgical manner.

With particular reference to FIGS. 25-27, the longitudinal connecting member assembly 501 is assembled to provide a pre-tensioned core 506 and pre-compressed spacer 510 and bumper 518 prior to implanting the assembly 501 in a patient. This is accomplished by first providing the anchor member 504 that has a core 506 that is longer in the axial direction AA than the core 506 illustrated in the drawing figures. The spacer 510 is first loaded onto the core 506 by inserting the core 506 end 544 into the bore defined by the inner surfaces 584 with the spacer end face 588 directed toward the buttress plate 546. The spacer 510 is moved along the core 506 until the surface 586 contacts the surface 558. The sleeve 512 is then threaded onto the core 506 with the face 576 of the plate 570 facing the end surface 589 of the spacer 510. The core 506 is received in the bore defined by the inner planar surfaces 564 and 566 and the sleeve 512 is moved along the core 506 until the plate surface 576 abuts the spacer surface 589. The bumper 518 is thereafter loaded onto the core 506 by inserting the core 506 end 544 into the bore defined by the inner surfaces 594 with the face 596 facing the toward the surface 578 of the sleeve 512. The bumper 518 is moved along the core 506 until the surface 596 contacts the surface 578. The crimping member 520 is thereafter loaded onto the core 506 by inserting the core 506 end 544 into the bore defined by the inner surfaces 604 with the face 606 facing the toward the surface 598 of the bumper 518. The crimping member 520 is moved along the core 506 until the surface 606 contacts the surface 598. It is noted that due to the symmetrical nature of the sleeve 512, the spacer 514, the bumper 518 and the crimping member 520, these components may be loaded onto the core 506 from either side thereof. However, if, as in the illustrated embodiment, the bone anchor attachment portion 508, the spacer 510 and the sleeve 512 are not of square cross-section, such components 508, 510 and 512 are assembled on the core 506 in alignment with the surfaces 548, 580 and 560 being loaded on the core to be in parallel planes. As illustrated in FIGS. 25 and 26, in the illustrated embodiment, such alignment places the surfaces 548 and 560 in substantially the same plane. Likewise, such assembly places the surfaces 550, 582 and 562 in parallel with the surfaces 550 and 562 being in substantially the same plane.

After the crimping member 520 is loaded onto the core 506, manipulation tools (not shown) are used to grasp the core 506 near the end 544 and at the bone anchor attachment portion 508, placing tension on the core 506. Furthermore, the spacer 510, the sleeve 512, the bumper 518 and the crimping member 520 are moved toward the buttress plate 540 and into contact with one another. Alternatively, or in addition, axial compressive force is placed on the components loaded on the core 506, followed by deforming the crimping member at the crimp grooves 610 and against the core 506. When the manipulation tools are released, the crimping member 520, now firmly and fixedly attached to the core 506 holds the spacers 510 and the bumper 518 in compression and the spacers and bumper place axial tension forces on the core 506, resulting in a dynamic relationship between the core 506 and the spacer 510 and bumper 518. The tension on the core 506 is advantageously balanced and uniform as the spacer 510 is slidable with respect to the core 506, but also are limited by the buttress plate of the anchor member 504 and end plate of the sleeve 512. Furthermore, the bumper 518 that is compressed between the sleeve surface 578 and the crimping member surface 606 is also slidable with respect to the core 506. The spacer 510 and the bumper 518 place a distractive force on the core 506 along the axis AA and between the buttress plate 546 and the crimping member 520, but also are movable with respect to the core 506, thus being able to respond to jolting and other body movements and thereafter spring back into an originally set location.

The sleeve 512 may compress slightly, but is more rigid than the spacer 510 and bumper 518 and thus keeps the spacers 510 and bumper 518 in an approximate desired axially spaced relation. However, the spacer 510 also advantageously slides along the core 506 in response to outside forces. The core 506 is then trimmed to be approximately flush with the end surface 608 of the crimping member 520.

With reference to FIG. 38, the pre-loaded connecting member assembly 501 is eventually positioned in an open, percutaneous or other less invasive manner in cooperation with the at least two bone screws 525 with the spacer 510 being disposed between and spaced from the bone screws 525 and with the portion 508 and sleeve 512 each being located within a squared-off U-shaped channel of a cooperating bone screw receiver 531. Once a desired position is attained, a closure structure 527 is then inserted into and advanced between the arms of each of the bone screw receivers 531 until appropriately tightened.

The assembly 501 is thus substantially dynamically loaded and oriented relative to the cooperating vertebra, providing relief (e.g., shock absorption) and protected movement with respect to flexion, extension, distraction and compressive forces placed on the assembly 501 and the connected bone screws 525. The slender core extension 506 allows for some twisting providing some relief for torsional stresses. However, the fact that the core 506 is of a non-round cross-section and cooperates with through bores of the other assembly components that are also non-round and closely slidingly mate with the core 506 also advantageously provides limits to rotational or twisting movement of the assembly 501 in response to torsional forces. Furthermore, the compressed spacer 510 places some limits on torsional movement as well as bending movement, to provide spinal support. The pre-loaded core 506 (in tension) and spacer 510 and bumper 518 (in compression) allow for compression and some extension of the assembly 501 located between the two bone screws 525, e.g., shock absorption.

If removal of the assembly 501 from any of the bone screw assemblies 525 is necessary, or if it is desired to release the assembly 501 at a particular location, disassembly is accomplished by using the driving tool (not shown) with a driving formation cooperating with the closure structure 527 internal drive or cooperating set screw internal drive to rotate and remove the closure structure 527 from the receiver 531. Disassembly is then accomplished in reverse order to the procedure described previously herein for assembly.

Eventually, if the spine requires more rigid support, the connecting member assembly 501 according to the invention may be removed and replaced with another longitudinal connecting member, such as a solid cylindrical or bar-like rod, having the same diameter or width as the width of the bar-like portion 508 and the sleeve 512, utilizing the same receivers 531 and the same or similar closure structures 527. Alternatively, if less support is eventually required, a less rigid, more flexible assembly, for example, an assembly 501 having components made of a more flexible material, but with the same size sleeves as the assembly 501, may replace the assembly 501, also utilizing the same bone screws 525.

With reference to FIGS. 39-44, another embodiment of a dynamic longitudinal connecting member of the invention, generally 701, includes an anchor member, generally 704, having an elongate segment or inner core 706 and a bone anchor attachment portion 708; an elastic spacer 710; a sleeve 716; an elastic bumper 718; and a crimping member 770; all substantially symmetrically aligned with respect to a central curvate axis BB of the anchor member 704 as unlike the core 506 of the assembly 501, the core 706 of the assembly 701 is bent primarily at a location near the portion 708. The elongate core 706 of the anchor member 704 is receivable within the spacer 710, the sleeve 716, the bumper 718 and the crimping member 720. Thus, the central curvate axis BB of the anchor member 704 is also the axis of the fully assembled assembly 701. When fully assembled and fixed with all components fixed in position as shown in FIG. 39, the inner core 706 is in tension and the spacer 710 and the bumper 718 are in compression.

In the illustrated embodiment, the anchor member 704 is substantially similar to the anchor member 504 previously described herein with respect to the assembly 501. Therefore, the member 704 includes the core 706, the bone anchor attachment portion 708 and an integral buttress plate 746 identical or substantially similar in size and shape to the respective core 506, attachment portion 508 and buttress plate 546 of the anchor member 504 previously described herein. The member 704 differs from the member 504 only in the fact that the core 706 is bent adjacent the buttress plate 746.

The sleeve 712 is identical or substantially similar to the sleeve 512 illustrated in FIGS. 32 and 33 and previously described herein, having an outer planar surfaces 760 and 762, inner planar surfaces 764 and 766 defining a through bore and an end plate 770 identical or substantially similar to the respective outer surfaces 560 and 562, inner surfaces 564 and 566 and end plate 570 of the sleeve 512 previously described herein. The bumper 718 and the crimping member 720 are identical or substantially similar to the respective bumper 518 and the crimping member 520 previously described herein with respect to the assembly 501.

The spacer 710 is operatively located between the buttress plate 746 and the sleeve plate 770 in a manner similar to the spacer 510 located between the plates 546 and 570 of the assembly 501. The spacer 710 is also made from materials similar to the materials from which the spacer 10 is made. The spacer 710 further includes inner planar surfaces 784 and a flanged surface 786 forming a through bore for receiving the core 706, such surfaces 784 and 786 being substantially similar in form and function to the surfaces 584 and 586 previously described herein with respect to the spacer 510 with the exception that the through bore may be further modified to follow the curvature of the bent core 706. Also, the spacer 710 is of a different shape than the spacer 510. The spacer 710 includes a pair of opposed planar surfaces 790 that are trapezoidal in shape. The surfaces 790 run parallel to the through bore formed by the planar surfaces 784, such bore terminating at opposed load-bearing end surfaces 792 and 794. The surfaces 792 and 794 are not parallel, each directed toward one another and terminating at a small top (operatively posterior with respect to the spine) surface 796 and sloping in a direction away from one another at a larger bottom (operatively anterior) surface 798. It is noted that also according to the invention the surface 796 may be placed in an anterior position and the surface 798 placed in a posterior position with respect to the spine if desired to correct spinal kyphosis. In other embodiments of the invention the core 706 and spacer 710 may be bent, sized and shaped for the correction of other spinal deformities, such as scoliosis, for example.

Figure 43:
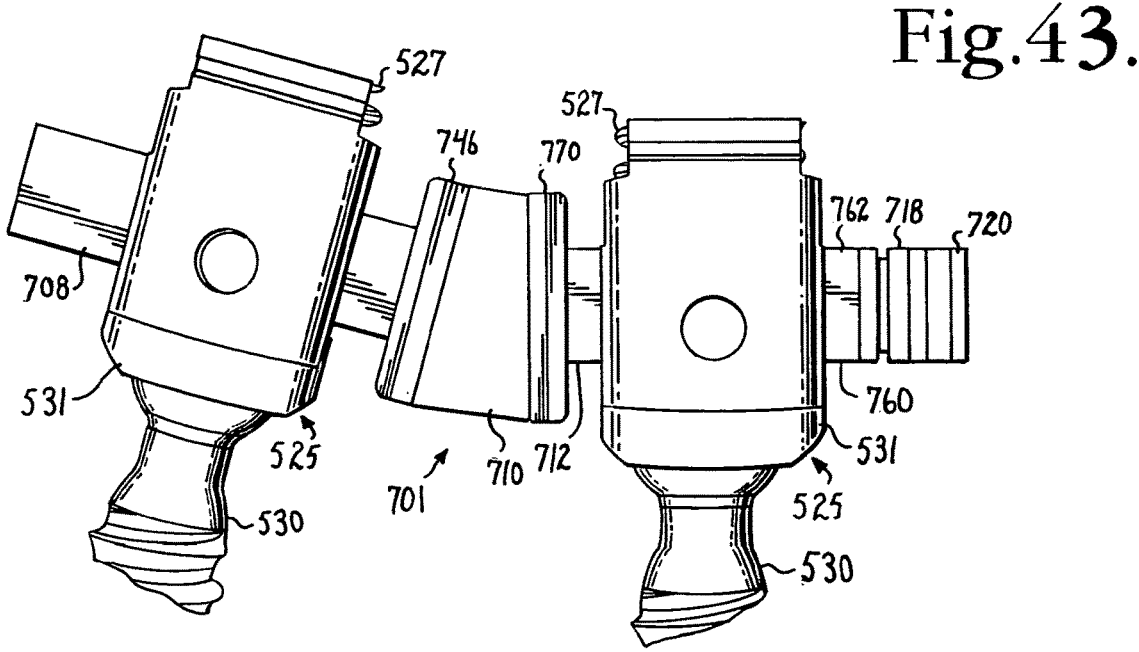
FIG. 43 is an enlarged and partial front elevational view of the assembly of FIG. 39 shown cooperating with a pair of bone screws.
Figure 44:
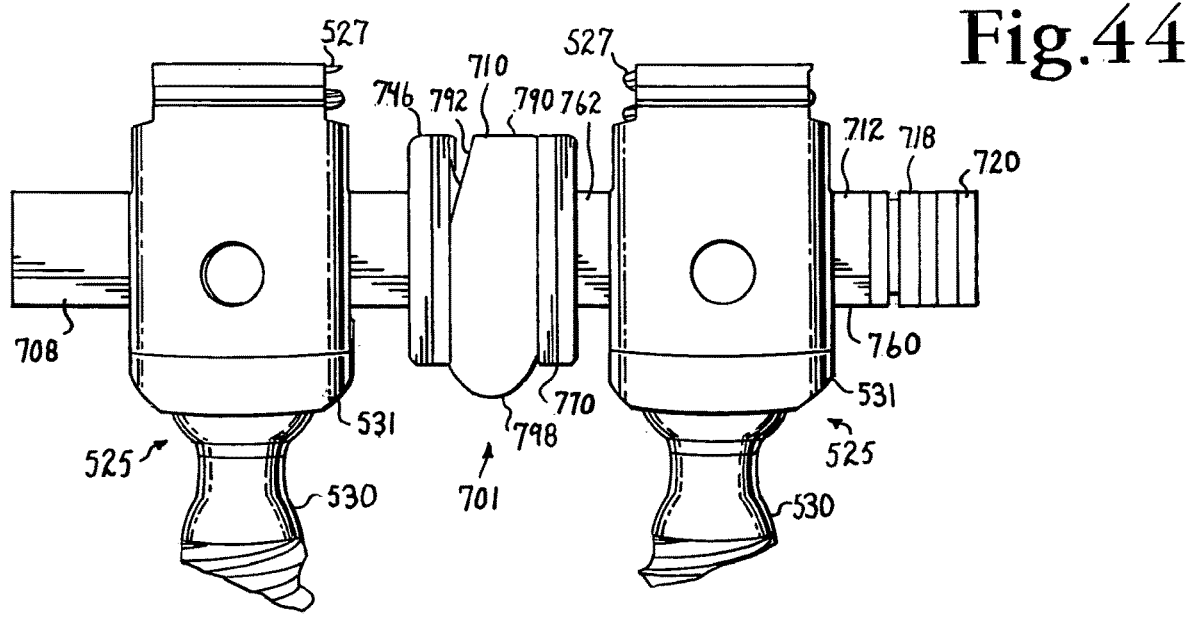
FIG. 44 is an enlarged and partial front elevational view similar to FIG. 43 showing the assembly in a loaded condition.
Figure 45:
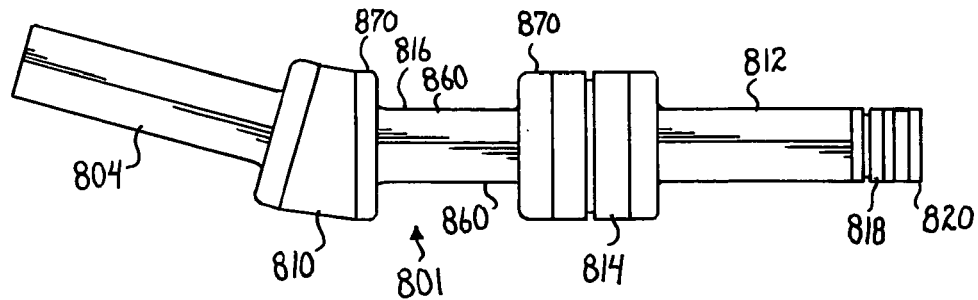
FIG. 45 is an enlarged front elevational view of a tenth embodiment of a dynamic fixation connecting member assembly according to the invention including an anchor member integral with an inner core, a first elastic spacer with a trapezoidal face, a first sleeve, a second elastic spacer, a second sleeve, an elastic bumper and a crimping member.
Figure 46:
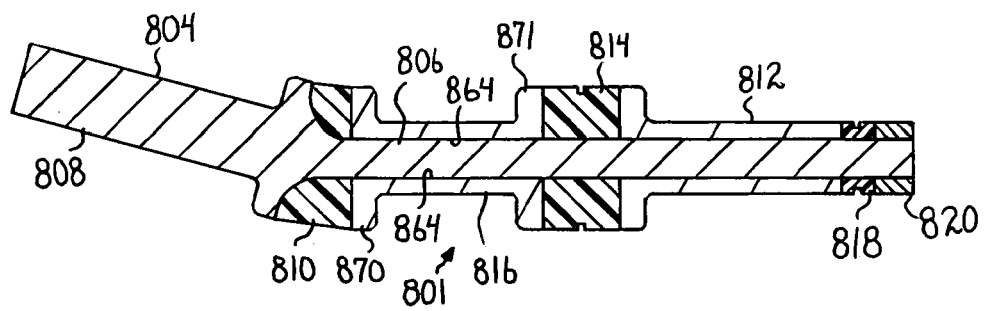
FIG. 46 is an enlarged front elevational view similar to FIG. 45 with portions broken away to show the detail thereof.
Figure 47:
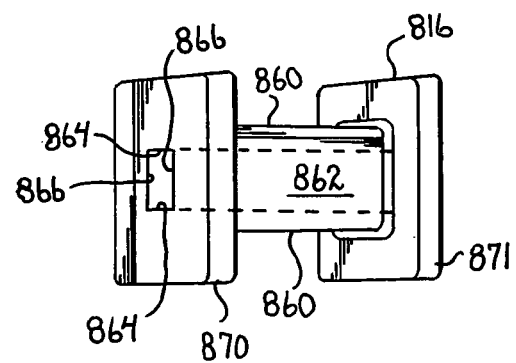
FIG. 47 is an enlarged perspective view of the first sleeve of FIG. 45.

The assembly 701 is assembled in a manner substantially similar to the manner of assembly previously described herein with respect to the assembly 501. Therefore, the core 706 is first received within a through bore of the spacer 710 formed by the surfaces 784, then within the inner planar surfaces 764 and 766 of the sleeve 712, followed by an inner through bore of the bumper 718 and then an inner through bore of the crimping member 720. Similar to what has been described previously with respect to the assembly 1, the core 706 is initially of a longer length measured along the axis BB than is shown in the drawing figures, allowing for a manipulation tool to grasp the core 706 near an end thereof that extends through the crimping member bore. The core 706 is tensioned and/or the spacer 710 and bumper 720 are compressed, followed by deformation of the crimping member 720 against the core 706. The core 706 is then trimmed substantially flush to the crimping member 720. The assembly is now in dynamic relationship with the core 706 being in tension while the spacer 710 that is slidable with respect to the core 706 is compressed between the plates 746 and 770 and the bumper 718 that is also slidable with respect to the core 706 is compressed between the sleeve 712 and the crimping member 720; the spacer 710 and the bumper 718 placing a distractive force on the core 706 along the axis BB and between the buttress plate 746 and the crimping member 720. The assembly 701 may then be implanted, cooperating with a pair of bone screws 525 as illustrated in FIG. 43 and as previously described herein with respect to the assembly 501. Unlike the assembly 501 illustrated in FIG. 38 the bent core 706 and cooperating trapezoidal spacer 710 provide additional support or correction to a spine, for example, when correcting spinal lordosis. With reference to FIG. 44, the assembly 701 and cooperating bone screws 525 of FIG. 43 are shown under a load that causes the core 706 to straighten and further compresses the spacer 710 resulting in a bulging of the flexible spacer at the anterior surface 798.

With reference to FIGS. 45-49, another embodiment of a dynamic longitudinal connecting member assembly, generally 801 is illustrated. The assembly 801 includes an anchor member 804 having an inner core 806 and a bone anchor attachment portion 808; a trapezoidal spacer 810, a sleeve 812, a second spacer 814, a second sleeve 816, a bumper 818 and a crimping member 820. The illustrated spacer 810, sleeve 812, bumper 818 and crimping member 820 are identical or substantially similar to the respective spacer 710, sleeve 712, bumper 718 and crimping member 720 previously described herein with respect to the assembly 701. The anchor member 804 is identical to the anchor member 704 with the exception that the bone anchor attachment portion 808 is of a greater length to receive three bone screw receivers 531 therealong while the portion 708 is sized to receive two bone screw receivers 531. The second spacer 814 is substantially similar in shape and function as the spacer 510 previously described herein with respect to the assembly 501 with the exception that the through bore defined by the inner planar surfaces is uniform (see FIG. 46) and does not require a flared portion for cooperating with the core 806 as the spacer 814 is disposed along a uniform mid-section of the core 806.

The sleeve 816 is for the most part similar to the sleeve 812, the sleeve 712 and the sleeve 512 of the previously described embodiments, having outer planar surfaces 860 and 862, a rectangular cross-section, inner planar surfaces 864 and 866 defining a through bore for closely receiving the core 806 and an end plate 870 identical or substantially similar to the respective outer surfaces 560 and 562, inner surfaces 564 and 566 and end plate 570 of the sleeve 512 previously described herein with respect to the assembly 501. Additionally, the sleeve 816 has an opposite end plate 871 spaced from and parallel to the end plate 870.

Figure 48:
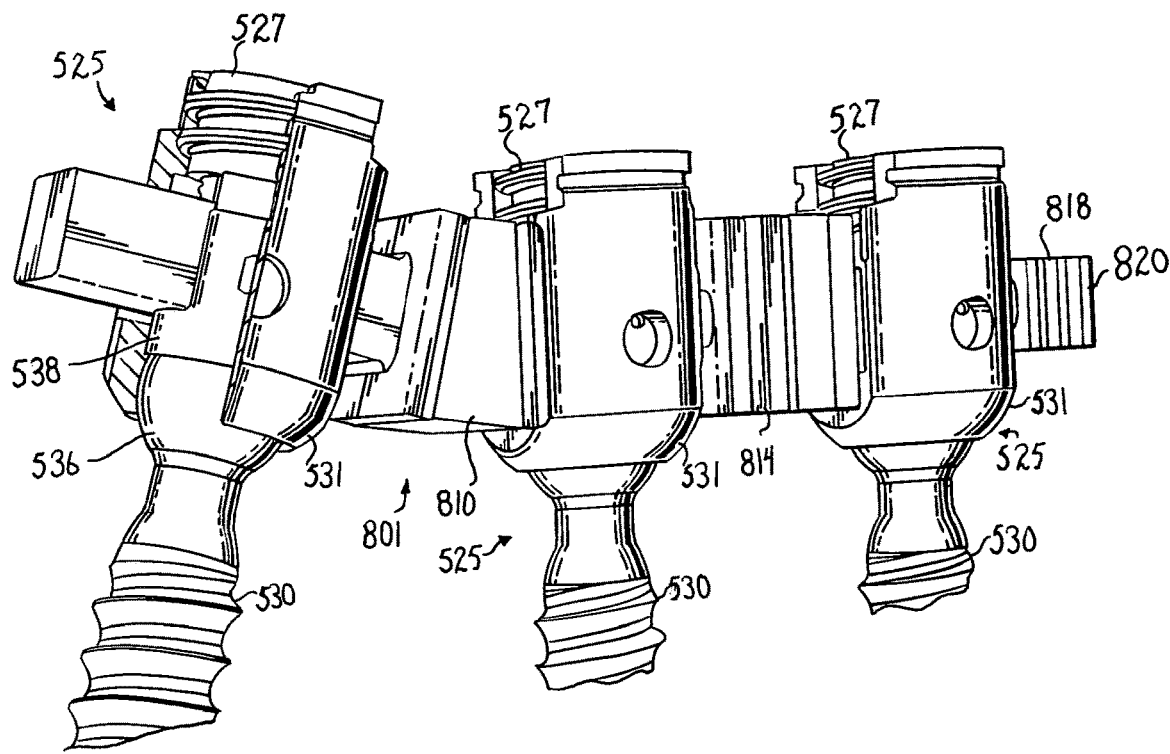
FIG. 48 is an enlarged and partial perspective view of the assembly of FIG. 45 shown cooperating with three bone screws and with portions broken away to show the detail thereof.
Figure 49:
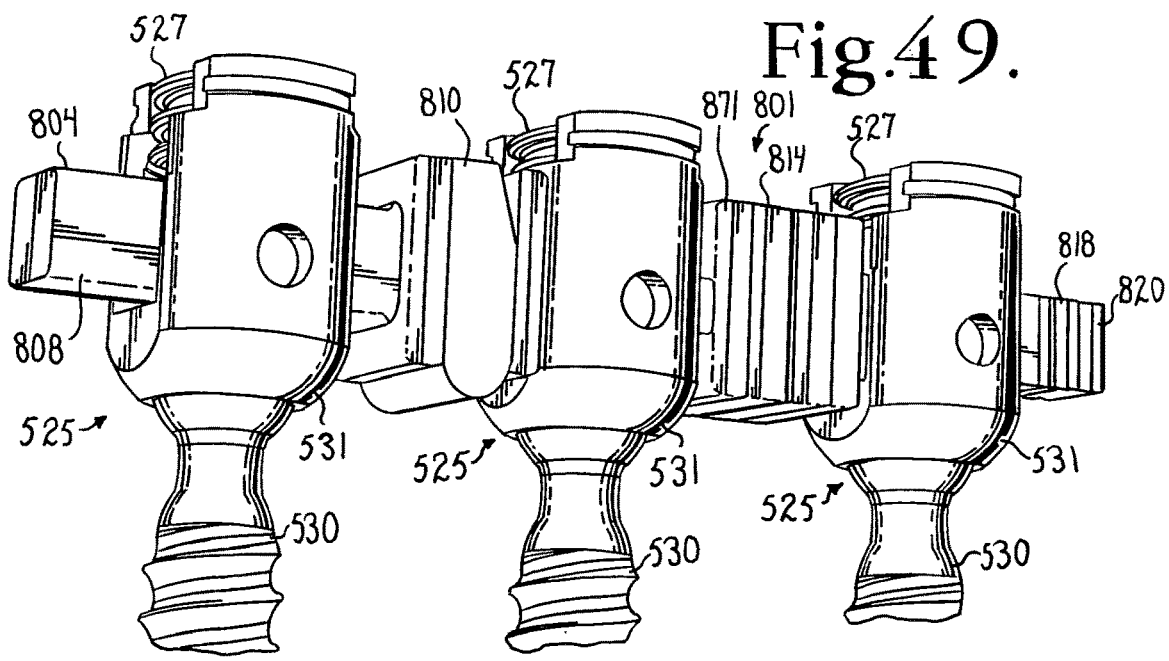
FIG. 49 is an enlarged and partial perspective view similar to FIG. 48 showing the assembly of FIG. 45 under a load.

The assembly 801 is assembled in a manner substantially similar to the manner of assembly previously described herein with respect to the assembly 701. The core 806 is first received within a through bore of the spacer 810, then within the inner planar surfaces 864 and 866 of the sleeve 816, followed by an inner through bore of the spacer 814 and then a through bore of the sleeve 812. Thereafter, the core 806 is received in an inner through bore of the bumper 818 and then an inner through bore of the crimping member 820. Similar to what has been described previously with respect to the assemblies 501 and 701, the core 806 is initially of a longer length than is shown in the drawing figures, allowing for a manipulation tool to grasp the core near an end thereof that extends through the crimping member bore. The core 806 is tensioned and/or the spacers 810 and 816 and the bumper 818 are compressed, followed by deformation of the crimping member 820 against the core 806. The core 806 is then trimmed substantially flush to the crimping member 820. The assembly is now in dynamic relationship with the core 806 being in tension while the spacers 810 and 816 that are slidable with respect to the core 806 are compressed and the bumper 818 that is also slidable with respect to the core 806 is compressed between the sleeve 812 and the crimping member 820; the spacers 810 and 816 and the bumper 818 placing a distractive force on the core 806 along an elongate axis thereof. The assembly 801 may then be implanted, cooperating with a three bone screws 525 as illustrated in FIG. 48 and as previously described herein with respect to the assembly 501. Unlike the assembly 501 illustrated in FIG. 38 the bent core 806 and cooperating trapezoidal spacer 810 provide additional support or correction to a spine, for example, when correcting spinal lordosis. With reference to FIG. 49, the assembly 801 and cooperating bone screws 525 of FIG. 48 are shown under a load that causes the core 806 to straighten and further compresses the spacer 810 resulting in a bulging of an anterior surface of the spacer 810.

It is foreseen that longitudinal connecting member assemblies according to the invention may be of a variety of lengths for cooperation with a plurality of bone screws 525, either along an attachment portion, such as the portion 808 or along dynamic portions that include one or more spacers and one or more sleeves, such as the sleeves 512, 712, 812 and 816 for attachment of a plurality of bone screws 525 or other bone anchors. It is foreseen that such sleeves may also be a variety of lengths for attachment to one or more bone anchors along a length of the individual sleeve.

Figure 50:
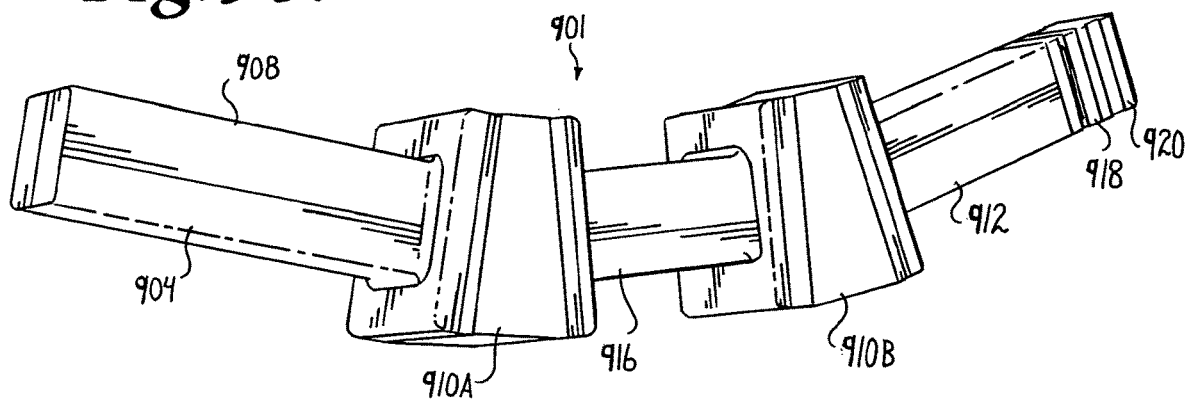
FIG. 50 is an enlarged perspective view of an eleventh embodiment of a dynamic fixation connecting member assembly according to the invention including an anchor member integral with an inner core, a first elastic spacer with a trapezoidal face, a first sleeve, a second elastic spacer with a trapezoidal face, a second sleeve, an elastic bumper and a crimping member.
Figure 51:
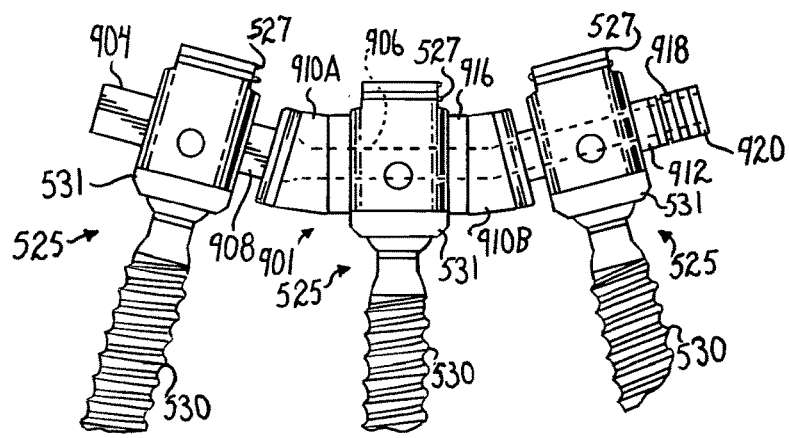
FIG. 51 is a reduced and partial front elevational view of the assembly of FIG. 50 shown cooperating with three bone screws.
Figure 52:
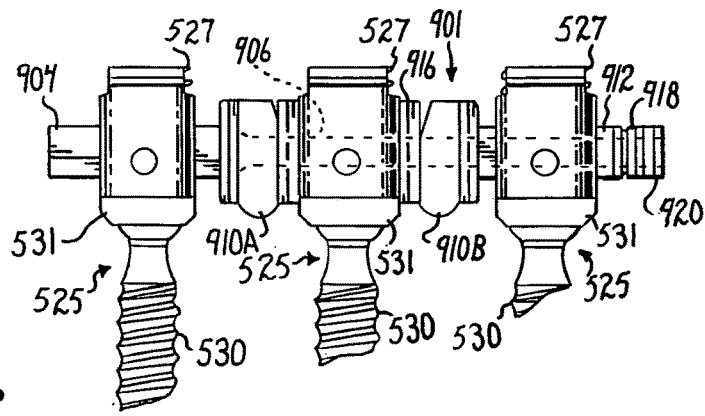
FIG. 52 is a partial front elevational view similar to FIG. 51 showing the assembly of FIG. 50 under a load.

As another example of an elongate dynamic connecting member of the invention for use with at least three bone screws 525, FIGS. 50-52 illustrate another embodiment of a dynamic longitudinal connecting member assembly, generally 901. The assembly 901 includes an anchor member 904 having an inner core 906 and a bone anchor attachment portion 908; first and second trapezoidal spacers 910A and 910B, a sleeve 912, a second sleeve 916, a bumper 918 and a crimping member 920. The illustrated trapezoidal spacers 910A and 910B are identical or substantially similar to the trapezoidal spacer 710 previously described herein with respect to the assembly 701. The second spacer 910B would not require an inner flared portion as such spacer is placed along a uniform mid-section of the core 906. The sleeves 912 and 916 are substantially similar to the respective sleeves 812 and 816 previously described herein with respect to the assembly 801. The bumper 918 and crimping member 920 are identical or substantially similar to the respective bumpers 518, 718 and 818 and crimping members 520, 720 and 820 previously described herein with respect to the assemblies, 501, 701 and 801. The anchor member 904 is identical to the anchor member 804 with the exception that the core 906 is bent at two locations corresponding to the operative placement of the trapezoidal spacers 910A and 910B.

The assembly 901 is assembled in a manner substantially similar to the manner of assembly previously described herein with respect to the assembly 801. The core 906 is first received within a through bore of the spacer 910, then within the inner planar surfaces defining the inner through bore of the sleeve 916, followed by an inner through bore of the spacer 910A and then a through bore of the sleeve 912. Thereafter, the core 906 is received in an inner through bore of the bumper 918 and then an inner through bore of the crimping member 920. Similar to what has been described previously with respect to the assemblies 501, 701 and 801, the core 906 is initially of a longer length than is shown in the drawing figures, allowing for a manipulation tool to grasp the core 906 near an end thereof that extends through the crimping member bore. The core 906 is tensioned and/or the spacers 910A and 910B and the bumper 918 are compressed, followed by deformation of the crimping member 920 against the core 906. The core 906 is then trimmed substantially flush to the crimping member 920. The assembly is now in dynamic relationship with the core 906 being in tension while the spacers 910A and 910B that are slidable with respect to the core 906 are compressed and the bumper 918 that is also slidable with respect to the core 906 is compressed between the sleeve 912 and the crimping member 920; the spacers 910A and 910B and the bumper 918 placing a distractive force on the core 946 along an elongate axis thereof. The assembly 901 may then be implanted, cooperating with a three bone screws 525 as illustrated in FIG. 51 and as previously described herein with respect to the assembly 501. Similar to the assembly 801, the bent core 906 and cooperating trapezoidal spacers 910A and 910B provide additional support or correction to a spine, for example, when correcting spinal lordosis. With reference to FIG. 52, the assembly 901 and cooperating bone screws 525 of FIG. 51 are shown under a load that causes the core 906 to straighten and further compresses the spacers 910A and 910B resulting in a bulging of anterior surfaces of the spacers 910A and 910B.

It is to be understood that while certain forms of the present invention have been illustrated and described herein, it is not to be limited to the specific forms or arrangement of parts described and shown.

The invention claimed is:

1. A medical implant assembly having a first bone attachment structure and a second bone attachment structure cooperating with a longitudinal connecting member, the longitudinal connecting member comprising:
    an anchor member having a rigid portion engageable to the first bone attachment structure and extending along a longitudinal axis;
    a flexible extension member integral with or fixedly attached to the rigid portion and extending therefrom along the longitudinal axis;
    a compressible outer spacer configured to be positioned between the first bone attachment structure and the second bone attachment structure;
    a sleeve configured to receive the flexible extension member in slidable relation with the second bone attachment structure;
    a stiff end structure having opposite outer tool engaging surfaces parallel with respect to each other, the stiff end structure compressibly attachable to the flexible extension member, the stiff end structure having a through bore configured to hold the flexible extension member in tension; and
    a bumper configured to be positioned between the second bone attachment structure and the stiff end structure, the bumper being spaced entirely outside of and spaced apart from the second bone attachment structure.

2. The medical implant assembly of claim 1, wherein the flexible extension member has a smaller diameter than the rigid portion.

3. The medical implant assembly of claim 1, wherein the flexible extension member is configured to be pre-tensioned along the longitudinal axis.

4. The medical implant assembly of claim 3, wherein the flexible extension member is configured to be pre-tensioned to a steady state length.

5. The medical implant assembly of claim 1, wherein the compressible outer spacer is configured to be held in compression by tensioning the flexible extension member.

6. The medical implant assembly of claim 1, wherein the flexible extension member is receivable within a non-threaded, non-tapered through-bore of the bumper and compressibly engageable therewith.

7. The medical implant assembly of claim 1, wherein the stiff end structure is configured to be in compressible engagement with the bumper.

8. The medical implant assembly of claim 1, wherein the bumper is configured to engage the sleeve.

9. The medical implant assembly of claim 1, wherein the bumper is elastic.

10. The medical implant assembly of claim 1, wherein the stiff end structure is configured to be positioned entirely outside the bumper.

11. The medical implant assembly of claim 1, wherein the anchor member rigid portion comprises a solid rod.

12. The medical implant assembly of claim 1, wherein the stiff end structure is configured to be accessible outside the first bone attachment structure and the second bone attachment structure for further tensioning of the flexible extension member.

13. The medical implant assembly of claim 1, wherein the sleeve is engageable to the second bone attachment structure.

14. The medical implant assembly of claim 1, wherein the through bore is smooth and non-threaded.

15. A medical implant assembly having a first bone attachment structure and a second bone attachment structure cooperating with a longitudinal connecting member, the longitudinal connecting member comprising:

an anchor member having a rigid portion engageable to the first bone attachment structure and extending along a longitudinal axis, the rigid portion having a first diameter;

a flexible extension member integral with or fixedly attached to the rigid portion and extending therefrom along the longitudinal axis, the flexible extension member having a second diameter smaller than the first diameter;

a sleeve configured to receive the flexible extension member in slidable relation with the second bone attachment structure;

a stiff end structure compressibly attachable to the flexible extension member, the stiff end structure having opposite outer tool engaging surfaces positioned parallel with respect to each other, the stiff end structure having a through bore configured to hold the flexible extension member in tension; and an elastic bumper configured to be positioned between the second bone attachment structure and the stiff end structure.

16. The medical implant assembly of claim 15, wherein a compressible outer spacer is configured to be held in compression by tensioning the flexible extension member.

17. The medical implant assembly of claim 16, wherein the compressible outer spacer is configured to be positioned between the first bone attachment structure and the second bone attachment structure.

18. The medical implant assembly of claim 15, wherein the through bore is smooth and non-threaded.

19. The medical implant assembly of claim 15, wherein the stiff end structure is configured to be in compressive engagement with the elastic bumper holding the flexible extension member in tension.

20. The medical implant assembly of claim 15, wherein the elastic bumper is spaced entirely outside of and spaced apart from the second bone attachment structure.

* * * * *